US006225532B1

United States Patent
Dixon et al.

(10) Patent No.: US 6,225,532 B1
(45) Date of Patent: May 1, 2001

(54) TOMATO CF-5 GENE ENCODING A DISEASE RESISTANCE POLYPEPTIDE

(75) Inventors: Mark S. Dixon, Southampton (GB); Kostas Hatzixanthis, Xanthi (GR); David A. Jones, Nicholls (AU); Jonathan D. Jones, Norwich (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 09/180,439

(22) PCT Filed: May 8, 1997

(86) PCT No.: PCT/GB97/01249

§ 371 Date: Dec. 17, 1998

§ 102(e) Date: Dec. 17, 1998

(87) PCT Pub. No.: WO97/43429

PCT Pub. Date: Nov. 20, 1997

(30) Foreign Application Priority Data

May 9, 1996 (GB) .................................................. 9609681
Sep. 24, 1996 (GB) .................................................. 9619924

(51) Int. Cl.[7] .............................. A01H 1/02; A01H 5/00; A01H 5/10; C12N 5/14; C12N 15/82
(52) U.S. Cl. ...................... 800/301; 435/320.1; 435/419; 536/23.6; 536/24.5; 800/265; 800/279; 800/286
(58) Field of Search ................................. 536/23.6, 24.5; 435/69.1, 320.1, 419, 468; 800/279, 286, 301, 265

(56) References Cited

FOREIGN PATENT DOCUMENTS

WO 95 31564   11/1995   (WO).
WO 96 30518   10/1996   (WO).

OTHER PUBLICATIONS

Dixon MS, et al. "The tomato Cf-5 disease resistance gene and six homologs show pronounced allelic variation leucine–rich repeat copy number." Plant Cell 10: 1915–1925, Nov. 1998.*

Dixon, M.S., et al.: "Solanum pimpinellifolium leucine rich repeat protein Cf-2.1 gene, complete cds." EMBL Sequence Database, REL. 47, Mar. 8, 1996, Acc. No. U42444.

Dixon, M.S., et al.: "Solanum pimpinellifolium leucine rich repeat protein Cf–2.2 gene, complete cds. " EMBL Sequence Database, REL. 47, Mar. 8, 1996, Acc. No. U42445.

Dixon M S et al: "The Tomato CF–2 Disease Resistance Locus Comprises Two Functional Genes Encoding Leucine–Rich Repeat Proteins" Cell, vol. 84, Feb. 9, 1996, pp. 451–459.

Hammond–Kosack K et al: "Characterisation of tomato genes that confer resistance to *Cladosporium fulvum*." Annual Meeting of The American Society of Plant Physiologists, Charlotte, North Carolina, USA, Jul. 29–Aug. 2, 1995. Plant Physiology (Rockville) 108 (2 Suppl.). 1995.

Dixon M S et al: "Cloning and characterisation of the Cf–2 disease and resistance gene, related family members and the corresponding null locus." Keystone Symposium On Signal Transduction In Plants, Hilton Head Island, South Carolina, USA, Mar. 29–Apr. 4, 1995. Journal of Cellular Biochemistry Supplement 0 (21A). 1995.

Dickinson M J et al: "Close Linkage Between the CF–2/CF–5 and MI Resistance Loci in Tomato" Molecular Plant–Microbe Interactions, vol. 6, No. 3, Jan. 1993, pp. 341–347.

Jones D A et al: "Two Complex Resistance Loci Revealed in Tomato by Classical and RFLP Mapping of The CF–2, CF–4, CF–5, and CF–9 Genes for Resistance To *Cladosporium fulvum*" Molecular Plant–Microbe Interactions, vol. 6, No. 3, Jan. 1, 1993, pp. 348–357.

* cited by examiner

*Primary Examiner*—Amy J. Nelson
(74) *Attorney, Agent, or Firm*—Nixon & Vanderhye

(57) ABSTRACT

The tomato Cf-5 gene has been cloned and its sequence provided, along with the encoded amino acid sequence. DNA encoding the polypeptide, may be introduced into plant cells and expressed, conferring pathogen resistance on plants comprising such cells and descendants thereof.

18 Claims, 17 Drawing Sheets

Figure 1A-(1)

```
   1 atcgatttta gagtcattgc aatttaattt tatcaaaata tttgagcatg
  51 aaaaatttga aatggaggtg tcataaaaat aaaatacccct ttacaacacg
 101 actttattga gttgacgata gttcaagtag ggaaaataaa taacttatta
 151 tttgaatata aaacttgcaa aaaaaaaaaa gtgatattca aatttaattc
 201 tgaccattat ctcttgatat tctttgctct tcatttattt gaatattcat
 251 ttttcaaaag ttccacatca taagacatca aatatcaagt aggtcccata
 301 aaaataaaat acccttctca acatgacaaa gaaagattga aaaatgacta
 351 acattttctc aaagacaaaa acaaaacatg tgagagaaga gaattttgaa
 401 ccaaatgtat tatacactaa gagtggtcat gatcattgtg tgataacaaa
 451 actattttgg caactttgac tcagtccttg gctaaattag acctctaaca
 501 caacagtcca aaagttgact tgagaatgac aacatttct tccctgatag
 551 caaccaaatt agcaaatttg gaaaaaacgt gtgtcttgtt gatctctaat
 601 tagtataagt aacgtacaat atcctattga atcggaaaca ataaactcac
 651 actatgatga tggttactag caaagtattc tcttcacttc agtttttcac
 701 tgttttctac ctctttacag ttgcatttgc ttcgactgag gaggcaactg
 751 ccctcttgac atggaaagca actttcaaga accagaataa ttcctttttg
 801 gcttcatgga cgacaagttc taatgcatgc aaggactggt atggagttgt
 851 atgcttgaat ggtagggtaa acacgttgaa tattacaaat gccagtgtca
 901 ttggtacact ttatgctttt ccattttcat ccctccctt tctcgagaat
 951 cttgatctta gcaacaacaa tatctctggt accattccac ctgagattgg
1001 taatctcaca aatcttgtct atcttgactt gaacaccaat cagatttcag
1051 gaacaattcc accacaaatc ggttcactag ccaagcttca gatcatccgc
1101 atatttaaca atcatttaaa tggctttatt cctgaagaaa taggttacct
1151 aaggtctctt actaagctat ctttggggtat caactttctt agtggttcta
1201 ttcctgcttc attgggcaat atgaccaact tgtctttttt atttctttat
1251 gaaaatcagc tttctggctt tattcctgaa gaaataggtt acctaaggtc
1301 tcttactaag ctatctttgg atatcaactt tcttagtggt tccattcctg
1351 cttcattggg gaatctgaac aacttgtctt ttttgtatct ttacaataat
1401 cagctttctg gctctattcc tgaagaaata ggttacctaa ggtcacttac
1451 taagctatct tgggtatca actttcttag tggttccatt cctgcttcat
1501 tggggaatct aaacaacttg tctaggttgg atctttacaa taataagctt
1551 tctggctcta ttcctgaaga aataggttac ctaaggtctc ttacttacct
1601 agatttgggt gagaatgctc ttaatggctc tattccttct tcattgggga
1651 atctaaacaa cttgtctagg ttggatcttt acaataataa gctttctggc
1701 tctattcctg aagaaatagg ttacctaagg tctcttactt acctagattt
1751 gggtgagaat gctcttaatg gctctattcc tgcttcattg gggaatctga
1801 acaacttgtt tatgttgtat ctttacaata atcagctttc tggctctatt
1851 cctgaagaaa taggttacct gagttctctt actgaactat atttgggtaa
1901 taactctctt aatggctcta ttcctgcttc attggggaat ctgacaacct
1951 tgtttatgtt gtatctttac aataatcagc tttctggctc tattcctgaa
2001 gaaataggtt acctgagttc tcttactgaa ctatttttgg gtaataactc
2051 tcttaatggc tctattcctg cttcattggg gaatctaaac aacttgtcta
2101 ggttgtatct ttacaataat cagctttctg gctctattcc tgcttcattt
2151 ggcaatatga gaaatctgca aactctgttt ctcagtgata acgatctcat
2201 tggggaaatt ccttcatttg tgtgcaattt gacatcactg gaagtgttgt
2251 atatgtcgag aaacaatttg aagggaaaag ttccgcaatg tttgggtaat
```

Figure 1A-(2)

```
2301  atcagtgacc ttcacatttt gtcgatgtca tctaatagtt tcagaggaga
2351  gctcccttca tctatttcca atttaacatc actaaaaata cttgattttg
2401  gcagaaacaa tctggaggga gcaataccac aatttttttgg caatattagt
2451  agcctccagg tttttgatat gcagaataac aaactttctg ggactcttcc
2501  aacaaatttt agcattggat gttcactgat aagtctcaac ttgcatggca
2551  atgaactagc agatgaaatc cctcggtctt tggacaattg caaaaagctg
2601  caagttcttg atttaggaga caatcaactc aacgacacat ttcccatgtg
2651  gttgggaact ttgccagagc tgagagtttt aaggttgaca tcgaataaat
2701  tgcatggacc tataagatca tcaggggctg aaatcatgtt tcctgatctc
2751  cgaatcatag atctctctcg caatgcattc tcgcaagact taccaacgag
2801  tctatttgaa catttgaaag ggatgaggac agttgataaa acaatggagg
2851  aaccaagtta tgaaagctat tacgatgact cggtggtagt tgtgacaaag
2901  ggattggagc ttgaaattgt gagaattctg tctttgtaca caattatcga
2951  tctttcaagc aacaaatttg aaggacatat tccttctgtc ctgggagatc
3001  tcattgcgat ccgtgtactt aatgtatctc ataatgcatt gcaaggctat
3051  ataccatcat cacttggaag tttatctata ctggaatcac tagaccttc
3101  gtttaaccaa ctttcgggag agataccaca acaacttgct tctcttacgt
3151  ttcttgaagt cttaaatctc tcccacaatt atctccaagg atgcatccct
3201  caaggacctc aattccgtac ctttgagagc aattcatatg aaggtaatga
3251  tggattacgt ggatatccag tttcaaaagg ttgtggcaaa gatcctgtgt
3301  cagagaaaaa ctatacagtg tctgcgctag aagatcaaga aagcaattct
3351  gaatttttca atgattttg gaaagcagct ctgatgggct atggaagtgg
3401  actgtgtatt ggcatatcca taatatatat cttgatctcg actggaaatc
3451  taagatggct tgcaagaatc attgaagaac tggaacacaa aattatcgtg
3501  caaaggagaa agaagcagcg aggtcaaaga aattacagaa gaagaaataa
3551  tcgcttctag acaagttacc aatacagaaa gatttgattt cagaacttca
3601  ggtattcaag ctaacctcta acacttatct tttttagttt attctaacaa
3651  ctaatatatg ttttttttt tatcaacaaa tacttattaa cgcttgagac
3701  aaattgctag taatcagttg gaagttgtga tatataacaa aggctaaaaa
3751  tttatagttg tgtgactcac tttcttattt ttccagattt tcaggagcca
3801  agaataagaa gacgctggtg taaaggattt gcttcttcct gtgttgcagc
3851  ttatgatgtt ggattagatt tttagtttta taagcttttc ttcagttggg
3901  aaaatgtaat attatgaatt ttgatgatat acaataaatg ttgtgtttat
3951  tgaatgatat gtatgcattt atcggatcc
```

Figure 1B-(1)

```
   1 atcgatttta gagtcattgc aatttaattt tatcaaaata tttgagcatg
  51 aaaaatttga aatggaggtg tcataaaaat aaaataccct ttacaacacg
 101 actttattga gttgacgata gttcaagtag ggaaaataaa taacttatta
 151 tttgaatata aaacttgcaa aaaaaaaaaa gtgatattca aatttaattc
 201 tgaccattat ctcttgatat tctttgctct tcatttattt gaatattcat
 251 ttttcaaaag ttccacatca taagacatca aatatcaagt aggtcccata
 301 aaaataaaat acccttctca acatgacaaa gaaagattga aaaatgacta
 351 acattttctc aaagacaaaa acaaaacatg tgagagaaga gaattttgaa
 401 ccaaatgtat tatacactaa gagtggtcat gatcattgtg tgataacaaa
 451 actattttgg caactttgac tcagtccttg gctaaattag acctctaaca
 501 caacagtcca aaagttgact tgagaatgac aacatttttct tccctgatag
 551 caaccaaatt agcaaatttg gaaaaaacgt gtgtcttgtt gatctctaat
 601 tagtataagt aacgtacaat atcctattga atcggaaaca ataaactcac
 651 actatgatga tggttactag caaagtattc tcttcacttc agttttcac
 701 tgttttctac ctctttacag ttgcatttgc ttcgactgag gaggcaactg
 751 ccctcttgaa atggaaagca actttcaaga accagaataa ttccttttg
 801 gcttcatgga cgacaagttc taatgcatgc aaggactggt atggagttgt
 851 atgcttgaat ggtagggtaa acacgttgaa tattacaaat gccagtgtca
 901 ttggtacact ttatgctttt ccattttcat ccctcccttt tctcgagaat
 951 cttgatctta gcaacaacaa tatctctggt accattccac ctgagattgg
1001 taatctcaca aatcttgtct atcttgactt gaacaccaat cagatttcag
1051 gaacaattcc accacaaatc ggttcactag ccaagcttca gatcatccgc
1101 atatttaaca atcatttaaa tggctttatt cctgaagaaa taggttacct
1151 aaggtctctt actaagctat ctttgggtat caactttctt agtggttcta
1201 ttcctgcttc attgggcaat atgaccaact tgtctttttt atttctttat
1251 gaaaatcagc tttctggctt tattcctgaa gaaataggtt acctaaggtc
1301 tcttactaag ctatctttgg atatcaactt tcttagtggt tccattcctg
1351 cttcattggg gaatctgaac aacttgtctt ttttgtatct ttacaataat
1401 cagctttctg gctctattcc tgaagaaata ggttacctaa ggtcacttac
1451 taagctatct ttgggtatca actttcttag tggttccatt cctgcttcat
1501 tggggaatct aaacaacttg tctaggttgg atctttacaa taataagctt
1551 tctggctcta ttcctgaaga aataggttac ctaaggtctc ttacttacct
1601 agatttgggt gagaatgctc ttaatggctc tattccttct tcattgggga
1651 atctaaacaa cttgtctagg ttggatcttt acaataataa gctttctggc
1701 tctattcctg aagaaatagg ttacctaagg tctcttactt acctagattt
1751 gggtgagaat gctcttaatg gctctattcc tgcttcattg gggaatctga
1801 acaacttgtt tatgttgtat ctttacaata atcagctttc tggctctatt
1851 cctgaagaaa taggttacct gagttctctt actgaactat atttgggtaa
1901 taactctctt aatggctcta ttcctgcttc attggggaat ctgaacaact
1951 tgtttatgtt gtatctttac aataatcagc tttctggctc tattcctgaa
2001 gaaataggtt acctgagttc tcttactgaa ctatttttgg gtaataactc
2051 tcttaatggc tctattcctg cttcattggg gaatctaaac aacttgtcta
2101 ggttgtatct ttacaataat cagctttctg gctctattcc tgcttcattt
2151 ggcaatatga gaaatctgca aactctgttt ctcagtgata acgatctcat
2201 tggggaaatt ccttcatttg tgtgcaattt gacatcactg gaagtgttgt
2251 atatgtcgag aaacaatttg aagggaaaag ttccgcaatg tttgggtaat
```

Figure 1B-(2)

```
2301  atcagtgacc ttcacatttt gtcgatgtca tctaatagtt tcagaggaga
2351  gctcccttca tctatttcca atttaacatc actaaaaata cttgattttg
2401  gcagaaacaa tctggaggga gcaataccac aattttttgg caatattagt
2451  agcctccagg tttttgatat gcagaataac aaactttctg ggactcttcc
2501  aacaaatttt agcattggat gttcactgat aagtctcaac ttgcatggca
2551  atgaactagc agatgaaatc cctcggtctt tggacaattg caaaaagctg
2601  caagttcttg atttaggaga caatcaactc aacgacacat ttcccatgtg
2651  gttgggaact ttgccagagc tgagagtttt aaggttgaca tcgaataaat
2701  tgcatggacc tataagatca tcaggggctg aaatcatgtt tcctgatctc
2751  cgaatcatag atctctctcg caatgcattc tcgcaagact taccaacgag
2801  tctatttgaa catttgaaag ggatgaggac agttgataaa acaatggagg
2851  aaccaagtta tgaaagctat tacgatgact cggtggtagt tgtgacaaag
2901  ggattggagc ttgaaattgt gagaattctg tctttgtaca caattatcga
2951  tctttcaagc aacaaatttg aaggacatat tccttctgtc ctgggagatc
3001  tcattgcgat ccgtgtactt aatgtatctc ataatgcatt gcaaggctat
3051  ataccatcat cacttggaag tttatctata ctggaatcac tagaccttc
3101  gtttaaccaa ctttcgggag agataccaca acaacttgct tctcttacgt
3151  ttcttgaagt cttaaatctc tcccacaatt atctccaagg atgcatccct
3201  caaggacctc aattccgtac ctttgagagc aattcatatg aaggtaatga
3251  tggattacgt ggatatccag tttcaaaagg ttgtggcaaa gatcctgtgt
3301  cagagaaaaa ctatacagtg tctgcgctag aagatcaaga aagcaattct
3351  gaattttca atgatttttg gaaagcagct ctgatgggct atggaagtgg
3401  actgtgtatt ggcatatcca taatatatat cttgatctcg actggaaatc
3451  taagatggct tgcaagaatc attgaagaac tggaacacaa aattatcgtg
3501  caaaggagaa agaagcagcg aggtcaaaga aattacagaa gaagaaataa
3551  tcgcttctag acaagttacc aatacagaaa gatttgattt cagaacttca
3601  ggtattcaag ctaacctcta acacttatct tttttagttt attctaacaa
3651  ctaatatatg tttttttttt tatcaacaaa tacttattaa cgcttgagac
3701  aaattgctag taatcagttg gaagttgtga tatataacaa aggctaaaaa
3751  tttatagttg tgtgactcac tttcttattt ttccagattt tcaggagcca
3801  agaataagaa gacgctggtg taaaggattt gcttcttcct gtgttgcagc
3851  ttatgatgtt ggattagatt tttagttta taagcttttc ttcagttggg
3901  aaaatgtaat attatgaatt ttgatgatat acaataaatg ttgtgtttat
3951  tgaatgatat gtatgcattt atcggatcc
```

Figure 2A

MMMVTSKVFSSLQFFTVFYLFTVAFASTEEATALLTWKATFKNQNNSFLA
SWTTSSNACKDWYGVVCLNGRVNTLNITNASVIGTLYAFPFSSLPFLENL
DLSNNNISGTIPPEIGNLTNLVYLDLNTNQISGTIPPQIGSLAKLQIIRI
FNNHLNGFIPEEIGYLRSLTKLSLGINFLSGSIPASLGNMTNLSFLFLYE
NQLSGFIPEEIGYLRSLTKLSLDINFLSGSIPASLGNLNNLSFLYLYNNQ
LSGSIPEEIGYLRSLTKLSLGINFLSGSIPASLGNLNNLSRLDLYNNKLS
GSIPEEIGYLRSLTYLDLGENALNGSIPSSLGNLNNLSRLDLYNNKLSGS
IPEEIGYLRSLTYLDLGENALNGSIPASLGNLNNLFMLYLYNNQLSGSIP
EEIGYLSSLTELYLGNNSLNGSIPASLGNLNNLFMLYLYNNQLSGSIPEE
IGYLSSLTELFLGNNSLNGSIPASLGNLNNLSRLYLYNNQLSGSIPASFG
NMRNLQTLFLSDNDLIGEIPSFVCNLTSLEVLYMSRNNLKGKVPQCLGNI
SDLHILSMSSNSFRGELPSSISNLTSLKILDFGRNNLEGAIPQFFGNISS
LQVFDMQNNKLSGTLPTNFSIGCSLISLNLHGNELADEIPRSLDNCKKLQ
VLDLGDNQLNDTFPMWLGTLPELRVLRLTSNKLHGPIRSSGAEIMFPDLR
IIDLSRNAFSQDLPTSLFEHLKGMRTVDKTMEEPSYESYYDDSVVVVTKG
LELEIVRILSLYTIIDLSSNKFEGHIPSVLGDLIAIRVLNVSHNALQGYI
PSSLGSLSILESLDLSFNQLSGEIPQQLASLTFLEVLNLSHNYLQGCIPQ
GPQFRTFESNSYEGNDGLRGYPVSKGCGKDPVSEKNYTVSALEDQESNSE
FFNDFWKAALMGYGSGLCIGISIIYILISTGNLRWLARIIEELEHKIIVQ
RRKKQRGQRNYRRRNNRF

Figure 2B

MMMVTSKVFSSLQFFTVFYLFTVAFASTEEATALLKWKATFKNQNNSFLA
SWTTSSNACKDWYGVVCLNGRVNTLNITNASVIGTLYAFPFSSLPFLENL
DLSNNNISGTIPPEIGNLTNLVYLDLNTNQISGTIPPQIGSLAKLQIIRI
FNNHLNGFIPEEIGYLRSLTKLSLGINFLSGSIPASLGNMTNLSFLFLYE
NQLSGFIPEEIGYLRSLTKLSLDINFLSGSIPASLGNLNNLSFLYLYNNQ
LSGSIPEEIGYLRSLTKLSLGINFLSGSIPASLGNLNNLSRLDLYNNKLS
GSIPEEIGYLRSLTYLDLGENALNGSIPSSLGNLNNLSRLDLYNNKLSGS
IPEEIGYLRSLTYLDLGENALNGSIPASLGNLNNLFMLYLYNNQLSGSIP
EEIGYLSSLTELYLGNNSLNGSIPASLGNLNNLFMLYLYNNQLSGSIPEE
IGYLSSLTELFLGNNSLNGSIPASLGNLNNLSRLYLYNNQLSGSIPASFG
NMRNLQTLFLSDNDLIGEIPSFVCNLTSLEVLYMSRNNLKGKVPQCLGNI
SDLHILSMSSNSFRGELPSSISNLTSLKILDFGRNNLEGAIPQFFGNISS
LQVFDMQNNKLSGTLPTNFSIGCSLISLNLHGNELADEIPRSLDNCKKLQ
VLDLGDNQLNDTFPMWLGTLPELRVLRLTSNKLHGPIRSSGAEIMFPDLR
IIDLSRNAFSQDLPTSLFEHLKGMRTVDKTMEEPSYESYYDDSVVVVTKG
LELEIVRILSLYTIIDLSSNKFEGHIPSVLGDLIAIRVLNVSHNALQGYI
PSSLGSLSILESLDLSFNQLSGEIPQQLASLTFLEVLNLSHNYLQGCIPQ
GPQFRTFESNSYEGNDGLRGYPVSKGCGKDPVSEKNYTVSALEDQESNSE
FFNDFWKAALMGYGSGLCIGISIIYILISTGNLRWLARIIEELEHKIIVQ
RRKKQRGQRNYRRRNNRF

Figure 5-(1)

```
   1  aaaatttgaa atggaggtgt cataaaata  aaatacccTT tacaacacga
  51  ctttattgag ttgacgatag ttcaagtagg gaaaataaat aacttattat
 101  ttgaatataa aacttgcaaa aaaaaaaaag tgatattcaa atttaattct
 151  gaccattatc tcttgatatt ctttgctctt catttatttg aatattcatt
 201  tttcaaaagt tccacatcat aagacatcaa atatcaagta ggtcccataa
 251  aaataaaata cccttctcaa catgacaaag aaagattgaa aaatgactaa
 301  cattttctca aagacaaaaa caaacatgt  gagagaagag aattttgaac
 351  caaatgtatt atacactaag agtggtcatg atcattgtgt gataacaaaa
 401  ctattttggc aactttgact cagtccttgg ctaaattaga cctctaacac
 451  aacagtccaa aagttgactt gagaatgaca acattttctt ccctgatagc
 501  aaccaaatta gcaaatttgg aaaaaacgtg tgtcttgttg atctttaatt
 551  agtataagtt acgtacaata tcctattgaa tcggaaacaa taaactcaaa
 601  ctatgatgat ggttactagc aaagtattct cttcacttca gttttcact
 651  gttttctacc tctttacagt tgcatttgct tcgactgagg aggcaactgc
 701  cctcttgaaa tggaaagcaa ctttcaagaa ccagaataat tccttttggg
 751  cttcatggac gacaagttct aatgcatgca aggactggta tggagttgta
 801  tgcttgaatg gtagggtaaa cacgttgaat attacaaatg ccagtgtcat
 851  tggtacactt tatgcttttc cattttcatc cctccctttt ctcgagaatc
 901  ttgatcttag caacaacaat atctctggta ccattccacc tgagattggt
 951  aatctcacaa atcttgtcta tcttgacttg aacaccaatc agatttcagg
1001  aacaattcca ccacaaatcg gttcactagc caagcttcag atcatccgca
1051  tatttaacaa tcatttaaat ggctttattc ctgaagaaat aggttaccta
1101  aggtctctta ctaagctatc tttgggtatc aactttctta gtggttctat
1151  tcctgcttca ttgggcaata tgaccaactt gtcttttta  tttctttatg
1201  aaaatcagct ttctggcttt attcctgaag aaataggtta cctaaggtct
1251  cttactaagc tatctttgga tatcaacttt cttagtggtt ccattcctgc
1301  ttcattgggg aatctgaaca acttgtcttt tttgtatctt tacaataatc
1351  agctttctgg ctctattcct gaagaaatag gttacctaag gtctcttact
1401  tacctagatt tgaaagagaa tgctcttaat ggctctattc ctgcttcatt
```

Figure 5-(2)

```
1451  ggggaatctg  aacaacttgt  ctaggttgta  tctttacaat  aatcagcttt
1501  ctggctctat  tcctgaagaa  ataggttact  tgagttctct  tactaatcta
1551  tatttgggta  ataactctct  tattggactt  attcctgctt  cattcggcaa
1601  tatgagaaat  ctgcaagctc  tgtttctcaa  tgataacaat  ctcattgggg
1651  aaattccttc  atttgtgtgc  aatttaacat  cactagaact  gttgtatatg
1701  ccgagaaaca  atttgaaggg  aaaagttccg  caatgtttgg  gtaatatcag
1751  tgaccttctg  gttttgtcaa  tgtcatctaa  tagtttcagt  ggagagctcc
1801  cttcatctat  ttccaattta  acatcactaa  aaatacttga  ttttggcaga
1851  aacaatctgg  agggagcaat  accacaatgt  tttggcaata  ttagtagcct
1901  ccaggttttt  gatatgcaga  ataacaaact  ttctgggact  cttccaacaa
1951  attttagcat  tggatgttca  ctgataagtc  tcaacttgca  tggcaatgaa
2001  ctagaggatg  aaatcccttg  gtctttggac  aattgcaaaa  agctgcaagt
2051  tcttgattta  ggagacaatc  aactcaacga  cacatttccc  atgtggttgg
2101  gaactttgcc  agagctgaga  gttttaaggt  tgacatcgaa  taaattgcat
2151  ggacctataa  gatcatcagg  ggctgaaatc  atgtttcctg  atcttcgaat
2201  catagatctc  tctcgcaatg  cattctcgca  agacttacca  acaagtctat
2251  ttgaacattt  gaaagggatg  aggacagttg  ataaaacaat  ggaggaacca
2301  agctatgaaa  tatattacga  ttcggttgta  gttgtgacaa  agggattgga
2351  gcttgaaatt  gtgagaattc  tgtctttgta  cacagttatc  gatctttcaa
2401  gcaacaaatt  tgaaggacat  attccttctg  tcctgggaga  tctcattgcg
2451  atccgtgtac  ttaatgtatc  tcataatgca  ttgcaaggct  atataccatc
2501  atcacttgga  agtttatcta  tactggaatc  actagacctt  tcgtttaacc
2551  aactttcggg  agagatacca  caacaacttg  cttctcttac  gtttcttgaa
2601  ttcttaaatc  tctcccacaa  ttatctccaa  ggatgcatcc  ctcaaggacc
2651  tcaattccgt  acctttgaga  gcaattcata  tataggtaat  gatggattac
2701  gtggatatcc  agtttcaaaa  ggttgtggca  agatcctgt   gtcagagaaa
2751  aactatacag  tgtctgcgct  agaagatcaa  gaaagcaatt  ctaaattttt
2801  caatgatttt  tggaaagcag  ctctgatggg  ctatggaagt  ggactgtgtt
2851  ttggcatatc  cataatatat  tcttgatct   cgactggaaa  tctaagatgg
```

Figure 5-(3)

```
2901  cttgcaagaa tcattgaaga actggaacac aaaattatta tgcaaaggag
2951  gaagaagcag cgaggtcaaa gaaattacag aagaagaaat aatcgcttct
3001  agacaagtta ccaaatacag aaagatttga tttcagaact tcaggtattc
3051  aagctaagct ctaacactta tctttttta gtttattcta acaactaata
3101  tatagttttt tttttatca acaatactt attaacactt gatacaaatt
3151  gctagtaatc agttggaagc tgtgatatat aacaaaggct aaaaatttat
3201  agttgtgtga ctcactttct tattttca gatttcagg agccaagaat
3251  tagaagacgc tggtgtaaag gatttgcttc ttcctatgtt gcagcttatg
3301  attgttggat ttgattttta gttttataag gttttcttca gttgggaaaa
3351  tgtaatattt tgaattttga tgatatacaa taaatgttgt gtttgttgaa
3401  tgatctgtat gcatttatcg gatcaataat actcacctca aagaatctaa
3451  gagagttagc gcacgataga agagatagaa catacaaaga agaatacatt
3501  acaaccttgg gctttactgg ttatcttaca ccccaaagct t
```

Figure 6

```
  1  MMMVTSKVFS SLQFFTVFYL FTVAFASTEE ATALLKWKAT FKNQNNSFLA
 51  SWTTSSNACK DWYGVVCLNG RVNTLNITNA SVIGTLYAFP FSSLPFLENL
101  DLSNNNISGT IPPEIGNLTN LVYLDLNTNQ ISGTIPPQIG SLAKLQIIRI
151  FNNHLNGFIP EEIGYLRSLT KLSLGINFLS GSIPASLGNM TNLSFLFLYE
201  NQLSGFIPEE IGYLRSLTKL SLDINFLSGS IPASLGNLNN LSFLYLYNNQ
251  LSGSIPEEIG YLRSLTYLDL KENALNGSIP ASLGNLNNLS RLYLYNNQLS
301  GSIPEEIGYL SSLTNLYLGN NSLIGLIPAS FGNMRNLQAL FLNDNNLIGE
351  IPSFVCNLTS LELLYMPRNN LKGKVPQCLG NISDLLVLSM SSNSFSGELP
401  SSISNLTSLK ILDFGRNNLE GAIPQCFGNI SSLQVFDMQN NKLSGTLPTN
451  FSIGCSLISL NLHGNELEDE IPWSLDNCKK LQVLDLGDNQ LNDTFPMWLG
501  TLPELRVLRL TSNKLHGPIR SSGAEIMFPD LRIIDLSRNA FSQDLPTSLF
551  EHLKGMRTVD KTMEEPSYEI YYDSVVVVTK GLELEIVRIL SLYTVIDLSS
601  NKFEGHIPSV LGDLIAIRVL NVSHNALQGY IPSSLGSLSI LESLDLSFNQ
651  LSGEIPQQLA SLTFLEFLNL SHNYLQGCIP QGPQFRTFES NSYIGNDGLR
701  GYPVSKGCGK DPVSEKNYTV SALEDQESNS KFFNDFWKAA LMGYGSGLCF
751  GISIIYFLIS TGNLRWLARI IEELEHKIIM QRRKKQRGQR NYRRRNNRF
```

Figure 7-(1)

```
   1  atcgatttta gagtcattgc aatttaattt tatcaaaata tttgagcatg
  51  aaaaatttga aatggaggtg tcataaaaat aaaatacccT ttacaacacg
 101  actttattga gttgacgata gttcaagtag ggaaaataaa taacttatta
 151  tttgaatata aaacttgcaa aaaaaaaaaa gtgatattca aatttaattc
 201  tgaccattat ctcttgatat tctttgctct tcatttattt gaatattcat
 251  ttttcaaaag ttccacatca taagacatca aatatcaagt aggtcccata
 301  aaataaaat accCttctca acatgacaaa gaaagattga aaaatgacta
 351  acattttctc aaagacaaaa acaaaacatg tgagagaaga gaattttgaa
 401  ccaaatgtat tatacactaa gagtggtcat gatcattgtg tgataacaaa
 451  actattttgg caactttgac tcagtccttg gctaaattag acctctaaca
 501  caacagtcca aaagttgact tgagaatgac aacatttTct tccctgatag
 551  caaccaaatt agcaaatttg gaaaaaacgt gtgtcttgtt gatctttaat
 601  tagtataagt tacgtacaat atcctattga atcggaaaca ataaactcaa
 651  actatgatga tggttactag caaagtattc tcttcacttc agttTttcac
 701  tgttttctac ctctttacag ttgcatttgc ttcgactgag gaggcaactg
 751  ccctcttgaa atggaaagca actttcaaga accagaataa ttccttttTg
 801  gcttcatgga cgacaagttc taatgcatgc aaggactggt atggagttgt
 851  atgcttgaat ggtagggtaa acacgttgaa tattacaaat gccagtgtca
 901  ttggtacact ttatgctttt ccatttTcat ccctcccttt tctcgagaat
 951  cttgatctta gcaacaacaa tatctctggt accattccac ctgagattgg
1001  taatctcaca aatcttgtct atcttgactt gaacaccaat cagatttcag
1051  gaacaattcc accacaaatc ggttcactag ccaagcttca gatcatccgc
1101  atatttaaca atcatttaaa tggctttatt cctgaagaaa taggttacct
1151  aaggtctctt actaagctat ctttgggtat caactttctt agtggttcta
1201  ttcctgcttc attgggcaat atgaccaact tgtctttttt atttctttat
1251  gaaaatcagc tttctggctt tattcctgaa gaaataggtt acctaaggtc
1301  tcttactaag ctatctttgg atatcaactt tcttagtggt tccattcctg
1351  cttcattggg aatctgaac aacttgtctt ttttgtatct ttacaataat
1401  cagctttctg gctctattcc tgaagaaata ggttacctca ggtcacttac
```

Figure 7-(2)

```
1451  taagctatct ttgggtatca actttcttag tggttccatt cctgcttcat
1501  tggggaatct aaacaacttg tctaggttgg atctttacaa taataagctt
1551  tctggctcta ttcctgaaga aataggttac ctaaggtctc ttacttacct
1601  agatttgggt gagaatgctc ttaatggctc tattcctgct tcattgggga
1651  atctaaacaa cttgtttatg ttgtatcttt acaataatca gctttctggc
1701  tctattcctg aagaatagg ttacctaagg tctcttactt acctagattt
1751  gggtgagaat gctcttaatg gctctattcc tgcttcattg gggaatctaa
1801  acaacttgtc taggttggat ctttacaata ataagctttc tggctctatt
1851  cctgaagaaa taggttacct aaggtctctt acttacctag atttgggtga
1901  gaatgctctt aatggctcta ttcctgcttc attggggaat ctgaacaact
1951  tgtttatgtt gtatctttac aataatcagc tttctggctc tattcctgaa
2001  gaaataggtt acctgagttc tcttactgaa ctatatttgg gtaataactc
2051  tcttaatggc tctattcctg cttcattggg gaatctgaac aacttgttta
2101  tgttgtatct ttacaataat cagctttctg gctctattcc tgaagaaata
2151  ggttacctga gttctcttac tgaactattt ttgggtaata actctcttaa
2201  tggctctatt cctgcttcat tggggaatct aaacaacttg tctaggttgt
2251  atctttacaa taatcagctt tctggctcta ttcctgcttc atttggcaat
2301  atgagaaatc tgcaaactct gtttctcagt gataacgatc tcattgggga
2351  aattccttca tttgtgtgca atttgacatc actggaagtg ttgtatatgt
2401  cgagaaacaa tttgaaggga aaagttccgc aatgtttggg taatatcagt
2451  gaccttcaca ttttgtcgat gtcatctaat agtttcagag gagagctccc
2501  ttcatctatt tccaatttaa catcactaaa aatacttgat tttggcagaa
2551  acaatctgga gggagcaata ccacaatttt ttggcaatat tagtagcctc
2601  caggtttttg atatgcagaa taacaaactt tctgggactc ttccaacaaa
2651  ttttagcatt ggatgttcac tgataagtct caacttgcat ggcaatgaac
2701  tagcagatga atccctcgg tctttggaca attgcaaaaa gctgcaagtt
2751  cttgatttag gagacaatca actcaacgac acatttccca tgtggttggg
2801  aactttgcca gagctgagag ttttaaggtt gacatcgaat aaattgcatg
2851  gacctataag atcatcaggg gctgaaatca tgtttcctga tctccgaatc
```

Figure 7-(3)

```
2901  atagatctct ctcgcaatgc attctcgcaa gacttaccaa cgagtctatt
2951  tgaacatttg aaagggatga ggacagttga taaaacaatg gaggaaccaa
3001  gttatgaaag ctattacgat gactcggtgg tagttgtgac aaagggattg
3051  gagcttgaaa ttgtgagaat tctgtctttg tacacaatta tcgatctttc
3101  aagcaacaaa tttgaaggac atattccttc tgtcctggga gatctcattg
3151  cgatccgtgt acttaatgta tctcataatg cattgcaagg ctatatacca
3201  tcatcacttg gaagtttatc tatactggaa tcactagacc tttcgtttaa
3251  ccaactttcg ggagagatac cacaacaact tgcttctctt acgtttcttg
3301  aagtcttaaa tctctcccac aattatctcc aaggatgcat ccctcaagga
3351  cctcaattcc gtacctttga gagcaattca tatgaaggta atgatggatt
3401  acgtggatat ccagtttcaa aaggttgtgg caaagatcct gtgtcagaga
3451  aaaactatac agtgtctgcg ctagaagatc aagaaagcaa ttctgaattt
3501  ttcaatgatt tttggaaagc agctctgatg ggctatggaa gtggactgtg
3551  tattggcata tccataatat atatcttgat ctcgactgga aatctaagat
3601  ggcttgcaag aatcattgaa gaactggaac acaaaattat cgtgcaaagg
3651  agaaagaagc agcgaggtca agaaattac agaagaagaa ataatcgctt
3701  ctagacaagt taccaataca gaaagatttg atttcagaac ttcaggtatt
3751  caagctaacc tctaacactt atctttttta gtttattcta acaactaata
3801  tatgtttttt ttttatcaa caaatactta ttaacgcttg agacaaattg
3851  ctagtaatca gttggaagtt gtgatatata acaaggcta aaaatttata
3901  gttgtgtgac tcactttctt attttccag attttcagga gccaagaata
3951  agaagacgct ggtgtaaagg atttgcttct tcctgtgttg cagcttatga
4001  tgttggatta gatttttagt tttataagct tttcttcagt tgggaaaatg
4051  taatattatg aatttgatg atatacaata aatgttgtgt ttattgaatg
4101  atatgtatgc atttatcgga tcc
```

Figure 8

```
   1  MMMVTSKVFS SLQFFTVFYL FTVAFASTEE ATALLKWKAT FKNQNNSFLA
  51  SWTTSSNACK DWYGVVCLNG RVNTLNITNA SVIGTLYAFP FSSLPFLENL
 101  DLSNNNISGT IPPEIGNLTN LVYLDLNTNQ ISGTIPPQIG SLAKLQIIRI
 151  FNNHLNGFIP EEIGYLRSLT KLSLGINFLS GSIPASLGNM TNLSFLFLYE
 201  NQLSGFIPEE IGYLRSLTKL SLDINFLSGS IPASLGNLNN LSFLYLYNNQ
 251  LSGSIPEEIG YLRSLTKLSL GINFLSGSIP ASLGNLNNLS RLDLYNNKLS
 301  GSIPEEIGYL RSLTYLDLGE NALNGSIPAS LGNLNNLFML YLYNNQLSGS
 351  IPEEIGYLRS LTYLDLGENA LNGSIPASLG NLNNLSRLDL YNNKLSGSIP
 401  EEIGYLRSLT YLDLGENALN GSIPASLGNL NNLFMLYLYN NQLSGSIPEE
 451  IGYLSSLTEL YLGNNSLNGS IPASLGNLNN LFMLYLYNNQ LSGSIPEEIG
 501  YLSSLTELFL GNNSLNGSIP ASLGNLNNLS RLYLYNNQLS GSIPASFGNM
 551  RNLQTLFLSD NDLIGEIPSF VCNLTSLEVL YMSRNNLKGK VPQCLGNISD
 601  LHILSMSSNS FRGELPSSIS NLTSLKILDF GRNNLEGAIP QFFGNISSLQ
 651  VFDMQNNKLS GTLPTNFSIG CSLISLNLHG NELADEIPRS LDNCKKLQVL
 701  DLGDNQLNDT FPMWLGTLPE LRVLRLTSNK LHGPIRSSGA EIMFPDLRII
 751  DLSRNAFSQD LPTSLFEHLK GMRTVDKTME EPSYESYYDD SVVVVTKGLE
 801  LEIVRILSLY TIIDLSSNKF EGHIPSVLGD LIAIRVLNVS HNALQGYIPS
 851  SLGSLSILES LDLSFNQLSG EIPQQLASLT FLEVLNLSHN YLQGCIPQGP
 901  QFRTFESNSY EGNDGLRGYP VSKGCGKDPV SEKNYTVSAL EDQESNSEFF
 951  NDFWKAALMG YGSGLCIGIS IIYILISTGN LRWLARIIEE LEHKIIVQRR
1001  KKQRGQRNYR RRNNRF
```

TOMATO CF-5 GENE ENCODING A DISEASE RESISTANCE POLYPEPTIDE

The present invention relates to pathogen resistance in plants and more particularly the identification and use of pathogen resistance genes. It is based on cloning of the tomato Cf-5 gene.

Plants are constantly challenged by potentially pathogenic microorganisms. Crop plants are particularly vulnerable, because they are usually grown as genetically uniform monocultures; when disease strikes, losses can be severe. However, most plants are resistant to most plant pathogens. To defend themselves, plants have evolved an array of both preexisting and inducible defences. Pathogens must specialize to circumvent the defence mechanisms of the host, especially those biotrophic pathogens that derive their nutrition from an intimate association with living plant cells. If the pathogen can cause disease, the interaction is said to be compatible, but if the plant is resistant, the interaction is said to be incompatible. Race specific resistance is strongly correlated with the hypersensitive response (HR), an induced response by which (it is hypothesized) the plant deprives the pathogen of living host cells by localized cell death at sites of attempted pathogen ingress.

It has long been known that HR-associated disease resistance is often (though not exclusively) specified by dominant genes (R genes). Flor. showed that when pathogens mutate to overcome such R genes, these mutations are recessive. Flor concluded that for R genes to function, there must also be corresponding genes in the pathogen, denoted avirulence genes (Avr genes). To become virulent, pathogens must thus stop making a product that activates R gene-dependent defence mechanisms (Flor, 1971). A broadly accepted working hypothesis, often termed the elicitor/receptor model, is that R genes encode products that enable plants to detect the presence of pathogens, provided said pathogens carry the corresponding Avr gene (Gabriel and Rolfe, 1990). This recognition is then transduced into the activation of a defence response.

Some interactions exhibit different genetic properties. *Helminthosporium carbonum* races that express a toxin (Hc toxin) infect maize lines that lack the Hm1 resistance gene. Mutations to loss of Hc toxin expression are recessive, and correlated with loss of virulence, in contrast to gene-for-gene interactions in which mutations to virulence are recessive. A major accomplishment was reported in 1992, with the isolation by tagging of the Hm1 gene (Johal and Briggs, 1992). Plausible arguments have been made for how gene-for-gene interactions could evolve from toxin-dependent virulence. For example, plant genes whose products were the target of the toxin might mutate to confer even greater sensitivity to the toxin, leading to HR, and the conversion of a sensitivity gene to a resistance gene. However, this does not seem to be the mode of action of Hm1, whose gene product inactivates Hc toxin.

Pathogen avirulence genes are still poorly understood. Several bacterial Avr genes encode hydrophilic proteins with no homology to other classes of protein, while others carry repeating units whose number can be modified to change the range of plants on which they exhibit avirulence (Keen, 1992; Long and Staskawicz, 1993). Additional bacterial genes (hrp genes) are required for bacterial Avr genes to induce HR, and also for pathogenicity (Keen, 1992; Long and Staskawicz, 1993). It is not clear why pathogens make products that enable the plant to detect them. It is widely believed that certain easily discarded Avr genes contribute to but are not required for pathogenicity, whereas other Avr genes are less dispensable (Keen, 1992; Long and Staskawicz, 1993). The characterization of one fungal avirulence gene has also been reported; the Avr9 gene of *Cladosporium fulvum*, which confers avirulence on *C. fulvum* races that attempt to attack tomato varieties that carry the Cf-9 gene, encodes a secreted cysteine-rich peptide with a final processed size of 28 amino acids but its role in compatible interactions is not clear (De Wit, 1992).

The technology for gene isolation based primarily on genetic criteria has improved dramatically in recent years, and many workers are currently attempting to clone a variety of R genes. Targets include (amongst others) rust resistance genes in maize, Antirrhinum and flax (by transposon tagging); downy mildew resistance genes in lettuce and Arabidopsis (by map based cloning and T-DNA tagging); *Cladosporium fulvum* (Cf) resistance genes in tomato (by tagging, map based cloning and affinity labelling with avirulence gene products); virus resistance genes in tomato and tobacco (by map based cloning and tagging); nematode resistance genes in tomato (by map based cloning); and genes for resistance to bacterial pathogens in Arabidopsis and tomato (by map based cloning).

The map based cloning of the tomato Pto gene that confers "gene-for-gene" resistance to the bacterial speck pathogen *Pseudomonas syringae* pv tomato (Pst) has been reported (Martin et al, 1993). A YAC (yeast artificial chromosome) clone was identified that carried restriction fragment length polymorphism (RFLP) markers that were very tightly linked to the gene. This YAC was used to isolate homologous cDNA clones. Two of these cDNAs were fused to a strong promoter, and after transformation of a disease sensitive tomato variety, one of these gene fusions was shown to confer resistance to Pst strains that carry the corresponding avirulence gene, AvrPto. These two cDNAs show homology to each other. Indeed, the Pto cDNA probe reveals a small gene family of at least six members, 5 of which can be found on the YAC from which Pto was isolated, and which thus comprise exactly the kind of local multigene family inferred from genetic analysis of other R gene loci.

Pto is atypical in encoding a small serine/threonine protein kinase which interacts directly with the avirulence determinant of Pst strains known as AvrPto (Tan et al., 1996, and Scofield et al., 1996).

Since the isolation of the Pto gene a number of other resistance genes have been isolated. The isolation of the tobacco mosaic resistance gene N from tobacco was reported by Whitham et al (1994). The isolation of the *Arabidopsis thaliana* gene for resistance to *Pseudomonas syringae* RPS2 was reported by Bent et al (1994) and by Mindrinos et al (1994). These genes probably encode cytoplasmic proteins that carry a P-loop and a leucine-rich repeat. The ligands with which they interact are uncharacterised and it is not known what other plant proteins they interact with to accomplish the defence response. Our own laboratory has reported the isolation of the tomato Cf-9 which confers resistance against the fungus *Cladosporium fulvum*. This is a subject of a previous patent application (PCT/GB94/02812 published as WO 95/18230) and has been reported in Jones et al (1994). Cf-9 and Avr9 sequences, and sequences of the encoded polypeptides are given in WO 95/18320 and Jones et al (1994). The Cf-2 gene is the subject of PCT/GB96/00785 filed Apr. 1, 1996 by John Innes Centre Innovations Limited. The Cf-4 gene is the subject of GB 9509575.8 filed May 11, 1995, to be used as priority for an International application by the same company. Sequences for Cf-9, Cf-2 and Cf-4 are disclosed in WO 95/31564.

We have now cloned Cf-5.

WO 93/11241 reports the sequence of a gene encoding a polygalacturonase inhibitor protein (PGIP) that has some homology with Cf-9 and, as we have now discovered, Cf-5 (the subject of the present invention). Cf-9, Cf-5 and others (Cf-4, -2 etc.) are termed by those skilled in the art "pathogen resistance genes" or "disease resistance genes". PGIP-encoding genes are not pathogen resistance genes. A pathogen resistance gene (R) enables a plant to detect the presence of a pathogen expressing a corresponding avirulence gene (Avr). When the pathogen is detected, a defence response such as the hypersensitive response (HR) is activated. By such means a plant may deprive the pathogen of living cells by localised cell death at sites of attempted pathogen ingress. On the other hand, the PGIP gene of WO 93/11241 (for example) is a gene of the kind that is induced in the plant defence response resulting from detection of a pathogen by an R gene.

Thus, a pathogen resistance gene may be envisaged as encoding a receptor to a pathogen-derived and Avr dependent molecule. In this way it may be likened to the RADAR of a plant for detection of a pathogen, whereas PGIP is involved in the defence the plant mounts to the pathogen once detected and is not a pathogen resistance gene. Expression of a pathogen resistance gene in a plant causes activation of a defence response in the plant. This may be upon contact of the plant with a pathogen or a corresponding elicitor molecule, though the possibility of causing activation by over-expression of the resistance gene in the absence of elicitor has been reported. The defence response may be activated locally, e.g. at a site of contact of the plant with pathogen or elicitor molecule, or systemically. Activation of a defence response in a plant expressing a pathogen resistance gene may be caused upon contact of the plant with an appropriate, corresponding elicitor molecule, e.g. as produced by a *Cladosporium fulvum* avr gene as discussed. The elicitor may be contained in an extract of a pathogen such as *Cladosporium fulvum*, or may be wholly or partially purified and may be wholly or partially synthetic. An elicitor molecule may be said to "correspond" if it is a suitable ligand for the R gene product to elicit activation of a defence response.

The "Cf-x"/"Avrx" terminology is standard in the art. The Cf resistance genes and corresponding fungal avirulence genes (Avr) were originally defined genetically as interacting pairs of genes whose measurable activities fall into mutually exclusive interacting pairs. Avr9 elicits a necrotic response on Cf-9 containing tomatoes but no response on Cf-S containing tomatoes, the moeity recognised by Cf-5 being different from that recognised by Cf-9.

Expression of Cf-5 function in a plant may be determined by investigating compatibility of various *C. fulvum* races.

A race of *C. fulvum* that carries functional copies of all known Avr genes (race 0) will grow (compatible) only on a tomato which lacks all the Cf genes. It will not grow (incompatible) on a plant carrying any functional Cf gene. If the *C. fulvum* race lacks a functional Avr5 gene (race 5) it will be able to grow not only on a plant lacking any Cf genes but also a plant carrying the Cf-5 gene. A race also lacking a functional Avr4 gene (race 4,5) will also be able to grow on a plant carrying the Cf-4 gene. A race only lacking a functional Avr4 gene (race 4) will not be able to grow on a plant carrying Cf-5. Similarly, a *C. fulvum* race 2 (lacking a functional Avr2 gene) will not be able to grow on a plant carrying a Cf-5 gene. Neither a race 4 nor a race 4,5 will be able to grow on a plant carrying any of the other Cf genes. Various races are commonly available in the art, e.g. from the Research Institute for Plant Protection (IPO-DLO), PO Box 9060, 6700 GW Wageningen, The Netherlands. A race 4 is available under accession number IP010379 and a race 2,4 available under Accession number IP050379.

We have now isolated a tomato gene, Cf-5, which confer resistance against the fungus *Cladosporium fulvum* and we have sequenced the DNA and deduced the amino acid sequence. The DNA sequence of the tomato Cf-5 gene is shown in FIG. 1 (SEQ ID NO:1 and SEQ ID NO:2) and the deduced amino acid sequence shown in FIG. 2 (SEQ ID NO:3 and SEQ ID NO:4). Two variant sequences are provided in these figures.

According to one aspect, the present invention provides a nucleic acid isolate encoding a pathogen resistance gene, the gene being characterized in that it comprises nucleic acid encoding the amino acid sequence shown in FIG. 2A (SEQ ID NO:3) or FIG. 2B (SEQ ID NO:4), or a fragment thereof. The nucleic acid isolate may comprise DNA, and may comprise the sequence shown in FIG. 1A or FIG. 1B, or a sufficient part to encode the desired polypeptide (eg. from the initiating methionine codon to the first in frame downstream stop codon). A suitable fragment is nucleotides 654–3558 of the sequence of FIG. 1A (SEQ ID NO:1) or FIG. 1B (SEQ ID NO:2). A further aspect of the invention provides a nucleic acid isolate encoding a pathogen resistance gene, or a fragment thereof, obtainable by screening a nucleic acid library with a probe comprising nucleotides of FIG. 1A (SEQ ID NO:1) or FIG. 1B (SEQ ID NO:2) or a fragment, derivative, mutant, variant or allele thereof, and isolating DNA which encodes a polypeptide able to confer pathogen resistance to a plant, such as resistance to *Cladosporium fulvum* (eg. expressing Avr5). The plant may be tomato. Suitable techniques are well known in the art.

Nucleic acid according to the present invention may encode the amino acid sequence shown in FIG. 2A (SEQ ID NO:3) or FIG. 2B (SEQ ID NO:4) or a mutant, variant, derivative or allele of the sequence provided. Preferred mutants, variants, derivatives and alleles are those which retain a functional characteristic of the protein encoded by the wild-type gene, especially the ability to confer pathogen resistance and most especially the ability to confer resistance against a pathogen expressing the Avr5 elicitor molecule. A fragment of the sequence, or an altered version thereof, may be employed which is able to confer recognition of Avr5, such as a fragment including the region LRR5 to LRR18, for example within the context of a synthetic construct comprising other domains of one or more resistance genes, including one or more domains required for induction of a resistance response upon recognition of Avr5.

Changes to a sequence, to produce a mutant, variant or derivative, may be by one or more of addition, insertion, deletion or substitution of one or more nucleotides in the nucleic acid, leading to the addition, insertion, deletion or subsitution of one or more amino acids. Of course, changes to the nucleic acid which make no difference to the encoded amino acid sequence are included.

A mutant, allele, variant or derivative amino acid sequence in accordance with the present invention may include within the sequence shown in FIG. 2A (SEQ ID NO:3) or FIG. 2B (SEQ ID NO:4), a single amino acid change with respect to the sequence shown in FIG. 2A (SEQ ID NO:3) or FIG. 2B (SEQ ID NO:4), e.g. at residue 36, or 2, 3, 4, 5, 6, 7, 8, or 9 changes, about 10, 15, 20, 30, 40 or 50 changes, or-greater than about 50, 60, 70, 80 or 90 changes. In addition to one or more changes within the amino acid sequence shown in FIG. 2A (SEQ ID NO:3) or FIG. 2B (SEQ ID NO:4), a mutant, allele, variant or derivative amino acid sequence may include additional amino acids at the C-terminus and/or N-terminus.

A sequence related to a sequence specifically disclosed herein shares homology with that sequence. Homology may be at the nucleotide sequence and/or amino acid sequence level. Preferably, the nucleic acid and/or amino acid sequence shares homology with the coding sequence or the sequence encoded by the nucleotide sequence of FIG. 1A (SEQ ID NO:1) or 1B (SEQ ID NO:2), preferably at least about 50%, or 60%, or 70%, or 80% homology, most preferably at least about 90%, 95%, 96%, 97%, 98% or 99% homology.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art, or, and this may be preferred, the standard program BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman Homology may be over the full-length of the relevant sequence shown herein, or may more preferably be over a contiguous sequence of about 20, 25, 30, 40, 50 or more amino acids or codons, compared with the relevant amino acid sequence or nucleotide sequence as the case may be.

Also provided by an aspect of the present invention is nucleic acid comprising a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a polypeptide able to confer pathogen resistance on a host, i.e., includes a pathogen resistance gene. Preferred conditions for hybridisation are familiar to those skilled in the art, but are generally stringent enough for there to be positive hybridisation between the sequences of interest to the exlucsion of other sequences.

Nucleic acid according to the present invention, for instance mutants, variants, derivatives and alleles of the specific sequences disclosed herein, may be distinguished from Cf-9, Cf-2 and/or Cf-4 by one or more of the following, or other features directly derivable from comparison of the Cf-5 amino acid sequence with the respective other sequence:

eliciting a defence response, in a plant expressing the nucleic acid, upon contact of the plant with Avr5 elicitor molecule, e.g. as provided by a *Cladosporium fulvum* race expressing Avr5 (available in the art);

eliciting a defence response, in a plant expressing the nucleic acid, upon contact of the plant with the *C. fulvum* race 4 deposited at and available from the Research Institute for Plant Protection (IPO-DLO), PO Box 9060, 6700 GW Wageningen, The Netherlands, under accession number IP010379, or an extract thereof, and eliciting a defence response in the plant upon its contact with the *C. fulvum* race 2,4 deposited at and available from the same institute under Accession number IP050379, or an extract thereof;

not eliciting a defence response, in a plant expressing the nucleic acid, upon contact of the plant with Avr9 elicitor molecule, e.g. as provided by a *Cladosporium fulvum* race or other organism expressing Avr9 (de Wit, 1992), the amino acid and encoding nucleic acid sequences of chimaeric forms of which are given for example in WO 95/18230 as SEQ ID NO 3 and in WO 95/31564 as SEQ ID NO 4;

not eliciting a defence response, in a plant expressing the nucleic acid, upon contact of the plant with Avr4 elicitor molecule, e.g. as provided by a *Cladosporium fulvum* race or other organism expressing Avr4, the amino acid and encoding nucleic acid sequences of which are given in WO 95/31564 SEQ ID NO. 13;

not eliciting a defence response, in a plant expressing the nucleic acid, upon contact of the plant with Avr2 elicitor molecule, e.g. as provided by a *Cladosporium fulvum* race or other organism expressing Avr2.

comprising the number of leucine rich repeats (LRR's) identifiable from the sequence information provided herein for Cf-5, 32.

A nucleic acid isolate according to the invention may encode a pathogen resistance gene whose expression in a plant can cause activation of a defence response in the plant, comprising a sequence of nucleotides encoding a polypeptide comprising the sequence of amino acids shown in FIG. 2A (SEQ ID NO:3) or FIG. 2B (SEQ ID NO:4).

The activation may be upon contact of the plant with a pathogen or corresponding elicitor molecule.

The sequence of nucleotides may comprise an encoding sequence shown in FIG. 1A (SEQ ID NO:1) or FIG. 1B (SEQ ID NO:2).

The nucleic acid may include a sequence of nucleotides comprising an allele, derivative, variant or mutant, by way of addition, insertion, deletion or substitution of one or more nucleotides, of an encoding sequence shown in FIG. 1A (SEQ ID NO:1) or FIG. 1B (SEQ ID NO:2). For example, the sequence may comprise nucleotides 654-3558 of FIG. 1A (SEQ ID NO:1) or FIG. 1B (SEQ ID NO:2).

Nucleic acid according to the present invention may encode a pathogen resistance gene whose expression in a plant can cause activation of a defence response in the plant, comprising a sequence of nucleotides encoding a polypeptide, the polypeptide comprising an amino acid sequence which comprises an allele, derivative, variant or mutant, by way of addition, insertion, deletion or substitution of one or more amino acids, of the amino acid sequence shown in FIG. 2A (SEQ ID NO:3) or FIG. 2B (SEQ ID NO:4).

The nucleic acid, which may contain for example DNA encoding the amino acid sequence of FIG. 2A (SEQ ID NO:3) or FIG. 2B (SEQ ID NO:4), as genomic or cDNA, may be in the form of a recombinant and preferably replicable vector, for example a plasmid, cosmid, phage or Agrobacterium binary vector. The nucleic acid may be under the control of an appropriate promoter or other regulatory elements for expression in a host cell such as a microbial, e.g. bacterial, or plant cell. In the case of genomic DNA, this may contain its own promoter or other regulatory elements and in the case of cDNA this may be under the control of an appropriate promoter or other regulatory elements for expression in the host cell.

Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology,* Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711–8721 (1984)) and Guerineau and Mullineaux (1993) (Plant transformation and expression vectors. In: Plant Molecular Biology Labfax (Croy RRD ed) Oxford, BIOS Scientific Publishers, pp 121–148).

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Nucleic acid molecules and vectors according to the resent invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may comprise cDNA, RNA, genomic DNA and may be wholly or artially synthetic. The term "isolate" encompasses all these possibilities. Where a DNA sequence is specified, e.g. with reference to a figure, unless context requires otherwise the RNA equivalent, with U substituted for T where it occurs, is encompassed.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711 - 87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture,* Academic Press), electroporation (EP 290395, WO 8706614 Gelvin Debeyser - see attached) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1–11.

Agrobacterium transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep.* 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO 92/14828). In particular, Agrobacterium mediated transformation is now emerging also as an highly efficient alternative transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewd in Vasil et al., *Cell Culture and Somatic Cell Genetics of Plants, Vol I, II and III, Laboratory Procedures and Their Applications,* Academic Press, 1984, and Weissbach and Weissbach, *Methods for Plant Molecular Biology,* Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

A Cf-5 gene and modified versions thereof (alleles, mutants, variants and derivatives thereof), and other nucleic acid provided herein may be used to confer resistance in plants, in particular tomatoes, to a pathogen such as *C. fulvum*. This may include cloned DNA from *Lycopersicon pimpinellifolium* which has the same chromosomal location as the Cf-5 gene or any subcloned fragment thereof. For this purpose nucleic acid such as a vector as described herein may be used for the production of a transgenic plant. Such a plant may possess pathogen resistance conferred by the Cf-5 gene.

The invention thus further encompasses a host cell transformed with such a vector, especially a plant or a microbial cell. Thus, a host cell, such as a plant cell, comprising nucleic acid according to the present invention is provided. Within the cell, the nucleic acid may be incorporated within the chromosome.

Also according to the invention there is provided a plant cell having incorporated into its genome nucleic acid, particularly heterologous nucleic acid, as provided by the present invention (e.g. a functional resistance gene), under operative control of a regulatory sequence for control of expression. The coding sequence may be operably linked to one or more regulatory sequences which may be heterologous or foreign to the gene, such as not naturally associated with the Cf-gene for its expression. The nucleic acid according to the invention may be placed under the control of an externally inducible gene promoter to place expression under the control of the user. A further aspect of the present invention provides a method of making such a plant cell involving introduction of nucleic acid or a suitable vector including the sequence of nucleotides into a plant cell and causing or allowing recombination between the vector and the plant cell genome to introduce the sequence of nucleotides into the genome. The invention extends to plant cells containing nucleic acid according to the invention as a result of introduction of the nucleic acid into an ancestor cell.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleic acid in question, may be provided. The transgene may be on an extragenomic vector or incorporated, preferably stably, into the genome. A heterologous gene may replace an endogenous equivalent gene, ie one which normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher or lower activity than wild-type, may be used in place of the endogenous gene. Nucleic acid heterologous, or exogenous or foreign, to a plant cell may be non-naturally occuring in cells of that type, variety or species. Thus, nucleic acid may include a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant.

The invention further provides a method of conferring pathogen resistance to a plant including expression of a heterologous nucleic acid sequence as discussed within cells of the plant.

The invention further provides a method of comprising expression from nucleic acid encoding the amino acid sequence of FIG. 2A (SEQ ID NO:3) or FIG. 2B (SEQ ID NO:4), or a mutant, variant, allele or derivative of the sequence, within cells of a plant (thereby producing the encoded polypeptide), following an earlier step of introduction of the nucleic acid into a cell of the plant or an ancestor thereof. Such a method may confer pathogen resistance on the plant. This may be used in combination with the Avr5 gene according to any of the methods described in W091/15585 (Mogen) or, more preferably, PCT/GB95/01075 (published as WO 95/31564), or any other gene involved in conferring pathogen resistance.

The Cf-5, CE-4, Cf-2 and Cf-9 genes function in a similar manner in that they confer a resistance to tomato that prevents the growth of tomato leaf mould *C. fulvum*. They, however, by recognition of different Avr products and have subtle differences in the speed with which they stop growth of the pathogen and stimulate a resistance response (Hammond-Kosack and Jones 1994; Ashfield et al 1994). These differences may be exploited to optimise applications disclosed herein.

Mutants have been isolated termed "required for Cladosporium resistance" or "rcr" in which a genetic lesion completely abolishes the resistance reaction as determined by the Cf-2 gene. These mutants do not affect the resistance reaction as determined by the Cf-9 resistance gene. This indicates that the Cf-2 and Cf-9 work via significantly different mechanisms. As Cf-5 is related to Cf-2, it is likely that the Cf-5 gene also works via this mechanism which is different from that for Cf-9.

A gene stably incorporated into the genome of a plant is passed from generation to generation to descendants of the plant, cells of which decendants may express the encoded polypeptide and so may have enhanced pathogen resistance. Pathogen resistance may be determined by assessing compatibility of a pathogen (eg. *Cladosporium fulvum*) or using recombinant expression of a pathogen avirulence gene, such as Avr-5 or delivery of the Avr-5 gene product.

Down-regulation of expression of a target gene may be achieved using anti-sense technology or "sense regulation" ("co-suppression").

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS USA* 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588, and U.S. Pat. No. 5,231,020.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be 500 nucleotides or less, possibly about 400 nucleotides, about 300 nucleotides, about 200 nucleotides, or about 100 nucleotides. It may be possible to use oligonucleotides of much shorter lengths, 14–23 nucleotides, although longer fragments, and generally even longer than 500 nucleotides are preferable where possible.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%., 15% or 20% or more mismatch between the sequence used and the target gene.

The invention further provides the use of fragments of a sequence according to the present invention, or a sequence complementary thereto as disclosed, in down-regulation of a target gene, such as a gene including a sequence shown in FIG. 1A (SEQ ID NO:1) or FIG. 1B (SEQ ID NO:2), or encoding an amino acid sequence shown in FIG. 2A (SEQ ID NO:3) or FIG. 2B (SEQ ID NO:4), or a mutant, allele, variant, derivative or homologue thereof, such as by antisense or sense suppression of expression (e.g. including at least transcription). Methods of down-regulating gene expression are thus provided.

Sequencing of the Cf-5 gene has shown that like the Cf-9 gene it includes DNA sequence encoding leucine-rich repeat (LRR) regions. The Cf-5 and Cf-9 genes contain all the same general features and as such form a new class of disease resistance genes separate from other disease resistance genes characterised to date. As discussed in WO 95/18230, and validated herein, the presence of LRRs may be characteristic of many pathogen resistance genes and the presence of LRRs may be used in identifying further pathogen resistance genes.

Furthermore, there are some striking homologies between Cf-9 and Cf-5. These homologies may also be used to identify further resistance genes of this class, for example using oligonucleotides (e.g. a degenerate pool) designed on the basis of sequences conserved (preferably at the amino acid level) between the Cf-9 and the Cf-5 genes.

The sequence information provided in FIG. 1A, 1B, 2A and/or 2B (SEQ ID NO:1, SEQ ID NO:2, SEQ ID NO:3 and SEQ ID NO:4, respectively) is sufficient for the person skilled in the art to clone a Cf-5 gene or homologue in accordance with the present invention.

A Cf-5 resistance gene or homologue in accordance with the present invention is obtainable by means of a method which includes providing a preparation of plant cell nucleic acid, e.g. tomato, (see e.g. Tigchelaar, 1984) providing a nucleic acid molecule having a nucleotide sequence shown in or complementary to a nucleotide sequence shown in FIG. 1A (SEQ ID NO:1) and/or FIG. 1B (SEQ ID NO:2), preferably from within the coding sequence (i.e. coding for an amino acid sequence shown in FIG. 2A (SEQ ID NO:3) or FIG. 2B (SEQ ID NO:4)), contacting nucleic acid in said preparation with said nucleic acid molecule under conditions for hybridisation of said nucleic acid molecule to any said gene or homologue in said preparation, and identifying said gene or homologue if present by its hybridisation with said nucleic acid molecule.

Hybridisation is generally followed by identification of successful hybridisation and isolation of nucleic acid which has hybridised, which may involve one or more steps of PCR.

Hybridisation of nucleic acid molecule to a Cf-5 gene or homologue may be determined or identified indirectly, e.g using a nucleic acid amplification reaction, particularly the polymerase chain reaction (PCR). PCR requires the use of two primers to specifically amplify target nucleic acid, so preferably two nucleic acid molecules with sequences characteristic of Cf-5 are employed. If RACE is used (see below) only one such primer may be needed.

Two primer which may be used for specific amplification of Cf-5 are OLIGO 2-5CF: GCTATCTTTGGGTAT-CAACTT (SEQ ID NO:9) and OLIGO 2-5CR: AGATGA-CATCGACAAAATGTG ((SEQ ID NO:10) the sequences or complementary sequences of which form part of FIG. 1A (SEQ ID NO:1) and FIG. 1B (SEQ ID NO:2)). Under appropriate conditions, such as an annealing temperature of around 55° C., such as 57° C. or 58° C., and with a suitable extension time, such as around 1 minute, these primers may be used in a PCR or other nucleic acid amplification reaction to amplify a 879 nucleotide fragment of Cf-5 and a 1023 nucleotide fragment of Hcr2-5D, which fragments may be used as or in the design of probes for obtaining the respective complete coding sequence from a plant that carries the Cf-5 gene. The size difference between the two fragments of Cf-5 and Hcr2-5D (144 nucleotides) reflects the additional two LRR's in the homologue. On a Cf-5 containing plant two bands are obtained on an electrophoretic gel of PCR products obtained using PCR with the conditions noted above, one for the Cf-5 gene and one for the Hcr2-5D homologue. Bands for other homologues are not identified on the gel.

PCR techniques for the amplification of nucleic acid are described in U.S. Pat. No. 4,683,195 and Saiki et al. *Science* 239: 487–491 (1988). PCR includes steps of denaturation of template nucleic acid (if double-stranded), annealing of primer to target, and polymerisation. The nucleic acid probed or used as template in the amplification reaction may be genomic DNA, cDNA or RNA. PCR may be used to amplify specific sequences from genomic DNA, specific RNA sequences and cDNA transcribed from mRNA. References for the general use of PCR techniques include Mullis et al, Cold Spring Harbor Symp. Quant. Biol., 51:263, (1987), Ehrlich (ed), PCR technology, Stockton Press, NY, 1989, Ehrlich et al, Science, 252:1643–1650, (1991), "PCR protocols; A Guide to Methods and Applications", Eds. Innis et al, Academic Press, New York, (1990).

Assessment of whether or not a PCR product corresponds to a homologue gene of interest may be conducted in various ways. A PCR band might contain a complex mix of products. Individual products may be cloned and each one individually screened. One possible mode of analysis is by transformation to assess function on introduction into a plant or plant cell of interest, though part of a gene amplified directly using the specific primers on the plant nucleic acid may not be sufficient for any function study.

A method involving use of PCR in obtaining nucleic acid according to the present invention may include providing a preparation of plant nucleic acid, e.g. tomato, providing a pair of nucleic acid molecule primers useful in (i.e. suitable for) PCR, at least one said primer having a sequence shown in or complementary to a sequence shown in FIG. 1A (SEQ ID NO:1) or FIG. 1B (SEQ ID NO:2), contacting nucleic acid in said preparation with said primers under conditions for performance of PCR, performing PCR and determining the presence or absence of an amplified PCR product. The presence of an amplified PCR product may indicate identification of a gene of interest or fragment thereof.

An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length. For optimum specificity, primers of 16–24 nucleotides in length may be preferred. Those skilled in the art are well versed in the design of primers for use processes such as PCR.

Some preferred oligonucleotides have a sequence set out in FIG. 1A (SEQ ID NO:1) or FIG. 1B (SEQ ID NO:2) (or complementary to such a sequence) or a sequence which differs from any of the sequences shown (or the complement) by addition, substitution, insertion or deletion of one or more nucleotides, but preferably without abolition of ability to hybridise selectively with a Cf-5 sequence shown in FIG. 1A (SEQ ID NO:1) or FIG. 1B (SEQ ID NO:2) or a complementary sequence, that is wherein the degree of homology of the oligonucleotide or polynucleotide with one of the sequences given is sufficiently high. Two oligos specific for Cf-5 and which do not amplify other close homologues from a Cf5 plant are disclosed above.

A gene or fragment thereof identified as being to which a said nucleic acid molecule hybridises, which may be an amplified PCR product, may be isolated and/or purified and may be subsequently investigated for ability to confer on a plant resistance to a pathogen. If the identified nucleic acid is a fragment of a gene, the fragment may be used (e.g. by probing and/or PCR) in subsequent cloning of the full-length gene, which may be a full-length coding sequence. Inserts may be prepared from partial cDNA clones and used to screen cDNA libraries. The full-length clones isolated may be subcloned into expression vectors and activity assayed by introduction into suitable host cells and/or sequenced. It may be necessary for one or more gene fragments to be ligated to generate a full-length coding sequence.

One or more changes to the coding sequence, by way of addition, deletion, substitution and/or insertion of one or more nucleotides, which may or may not be reflected by one or more changes at the amino acid level, may be made to a nucleotide sequence so-obtained.

Molecules found to be resistance genes may be used as such, i.e. to confer on a plant resistance to a pathogen. Nucleic acid obtained and obtainable using a method as disclosed herein is provided in various aspects of the present invention.

Nucleic acid isolated and/or purified from one or more cells of a plant, or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR), as discussed.

Test nucleic acid may be provided from a cell as genomic DNA, cDNA or RNA, or a mixture of any of these, preferably as a library in a suitable vector. Prior to any PCR that is to be performed, the complexity of a nucleic acid library may be reduced by creating a cDNA library for example using RT-PCR or by using the phenol emulsion reassociation technique (Clarke et al. (1992) NAR 20, 1289–1292) on a genomic library.

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolated hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes. For probing, preferred conditions are those which are stringent enough for there to be a simple pattern with a small number of hybridisations identified as positive which can be investigated further. It is well known in the art to increase stringency of hybridisation gradually until only a few positive clones remain. Suitable conditions would be achieved when a large number of hybridising fragments were obtained while the background hybridisation was low. Using these conditions nucleic acid libraries, e.g. cDNA libraries representative of expressed sequences, may be searched.

Those skilled in the art are well able to employ suitable conditions of the desired stringency for selective hybridisation, taking into account factors such as oligonucleotide length and base composition, temperature and so on.

According to a further aspect, the present invention provides a method of identifying a plant pathogen resistance gene comprising use of an oligonucleotide which comprises a sequence or sequences that are conserved between pathogen resistance genes such as Cf-9 and Cf-5, or Cf-5 and Cf-4 and/or Cf-2 to search for new resistance genes. Thus, a method of obtaining nucleic acid comprising a pathogen resistance gene (encoding a polypeptide able to confer pathogen resistance) is provided, comprising hybridisation of an oligonucleotide (details of which are discussed herein) or a nucleic acid molecular comprising such an oligonucleotide to target/candidate nucleic acid. Target or candidate nucleic acid may, for example, comprise a genomic or cDNA library obtainable from an organism known to encode a pathogen resistance gene. Successful hybridisation may be identified and target/candidate nucleic acid isolated for further investigation and/or use, as disclosed.

Preferred amino acid sequences suitable for use in the design of probes or PCR primers are sequences conserved (completely, substantially or partly) between polypeptides able to confer pathogen resistance such as those encoded by Cf-5 and Cf-9, and/or Cf-5 and Cf-2 and/or Cf-4.

On the basis of amino acid sequence information, oligonucleotide probes or primers may be designed, taking into account the degeneracy of the genetic code, and, where appropriate, codon usage of the organism from the candidate nucleic acid is derived.

Assessment of whether or not a PCR product corresponds to a resistance genes may be conducted in various ways, as discussed, and a PCR band may contain a complex mix of products. Individual products may be cloned and each sreened for linkage to known disease resistance genes that are segregating in progeny that showed a polymorphism for this probe. Alternatively, the PCR product may be treated in a way that enables one to display the polymorphism on a denaturing polyacrylamide DNA sequencing gel with specific bands that are linked to the resistance gene being preselected prior to cloning. Once a candidate PCR band has been cloned and shown to be linked to a known resistance gene, it may be used to isolate clones which may be inspected for other features and homologies to Cf-9, Cf-5 or other related gene. It may subsequently be analysed by transformation to assess its function on introduction into a disease sensitive variety of the plant of interest. Alternatively, the PCR band or sequences derived by analysing it may be used to assist plant breeders in monitoring the segregation of a useful resistance gene.

These techniques are of general applicability to the identification of pathogen resistance genes in plants. Examples of the type of genes that can be identified in this way include Phytophthora resistance in potatoes., mildew resistance and rust resistance in cereals such as barley and maize, rust resistance in Antirrhinum and flax, downy mildew resistance in lettuce and Arabidopsis, virus resistance in potato, tomato and tobacco, nematode resistance in tomato, resistance to bacterial pathogens in Arabidopsis and tomato and Xanthomonas resistance in peppers.

Once a pathogen resistance gene has been identified, it may be reintroduced into plant cells using techniques well known to those skilled in the art to produce transgenic plants. According to a further aspect, the present invention provides a DNA isolate encoding the protein product of a plant pathogen resistance gene which has been identified by use of the presence therein of LRRs or, in particular, by the technique defined above.

According to a yet further aspect, the invention provides transgenic plants, in particular crop plants, which have been engineered to carry pathogen resistance genes which have been identified by the presence of LRRs or by nucleic acid hybridisation as disclosed, or are otherwise provided by an embodiment of the present invention. Examples of suitable plants include tobacco, cucurbits, carrot, vegetable brassica, lettuce, strawberry, oilseed brassica, sugar beet, wheat, barley, maize, rice, soyabeans, peas, sorghum, sunflower, tomato, potato, pepper, chrysanthemum, carnation, poplar, eucalyptus and pine.

Modifications to these and further aspects and embodiments of the present invention will be apparent to those skilled in the art. All documents mentioned herein are incorporated by reference. The term "comprises" should generally be interpreted herein as meaning "includes", not "consisting of".

As already indicated, the present invention is based on the cloning and sequencing of the tomato Cf-5 gene and this experimental work is outlined below with reference to the following figures.

BRIEF DESCRIPTION OF THE DRAWINGS

FIGS. 1A–1B show the nucleotide sequence, including coding sequence, of cloned Cf-5 gene according to the present invention. The FIG. 1A (SEQ ID NO:1) and FIG. 1B (SEQ ID NO:2) sequences each represent a variant sequence of the other.

FIGS. 2A–2B show the amino acid sequence of CF-5 protein according to the invention. The FIG. 2A (SEQ ID NO:3) and FIG. 2B (SEQ ID NO:4) sequences each represent a variant sequence of the other, being respectively encoded by the encoding sequences of FIGS. 1A and 1B.

FIG. 5 shows the nucleic acid sequence of the clone Hcr2-5B gene (SEQ ID NO:5).

FIG. 6 shows the amino acid sequence of the HCR2-5B protein (SEQ ID NO:6).

FIG. 7 shows the nucleic acid sequence of the cloned Hcr2-5D gene (SEQ ID NO:7).

FIG. 8 shows the amino acid sequence of the HCR2-SD protein (SEQ ID NO:8).

CLONING OF THE CF-5 GENE

Figure 3:
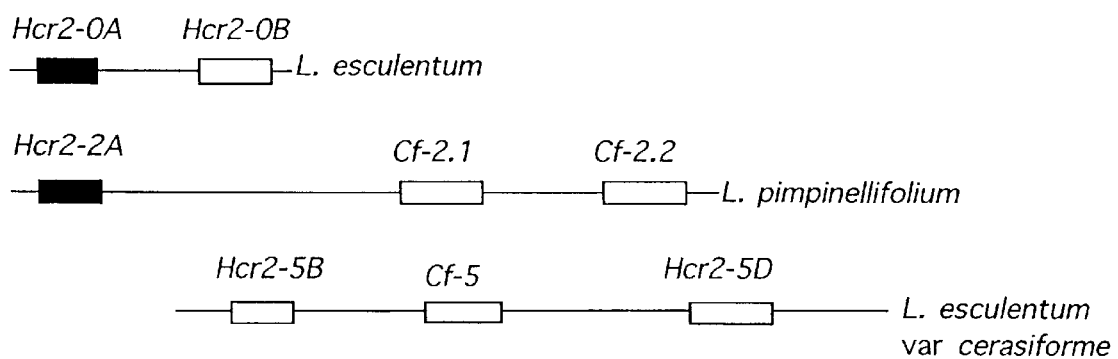
FIG. 3 shows a representation (not to scale) of the general structure of the genomic regions including the regions from the susceptible locus of Cf0, Cf2 and Cf5. The terminology "Hcr-x" is used as short-hand for "homologue of Cladosporium resistance gene x". The Cf-5 sequence of FIG. 1B is known also as Hcr2-5C.
Figure 4:
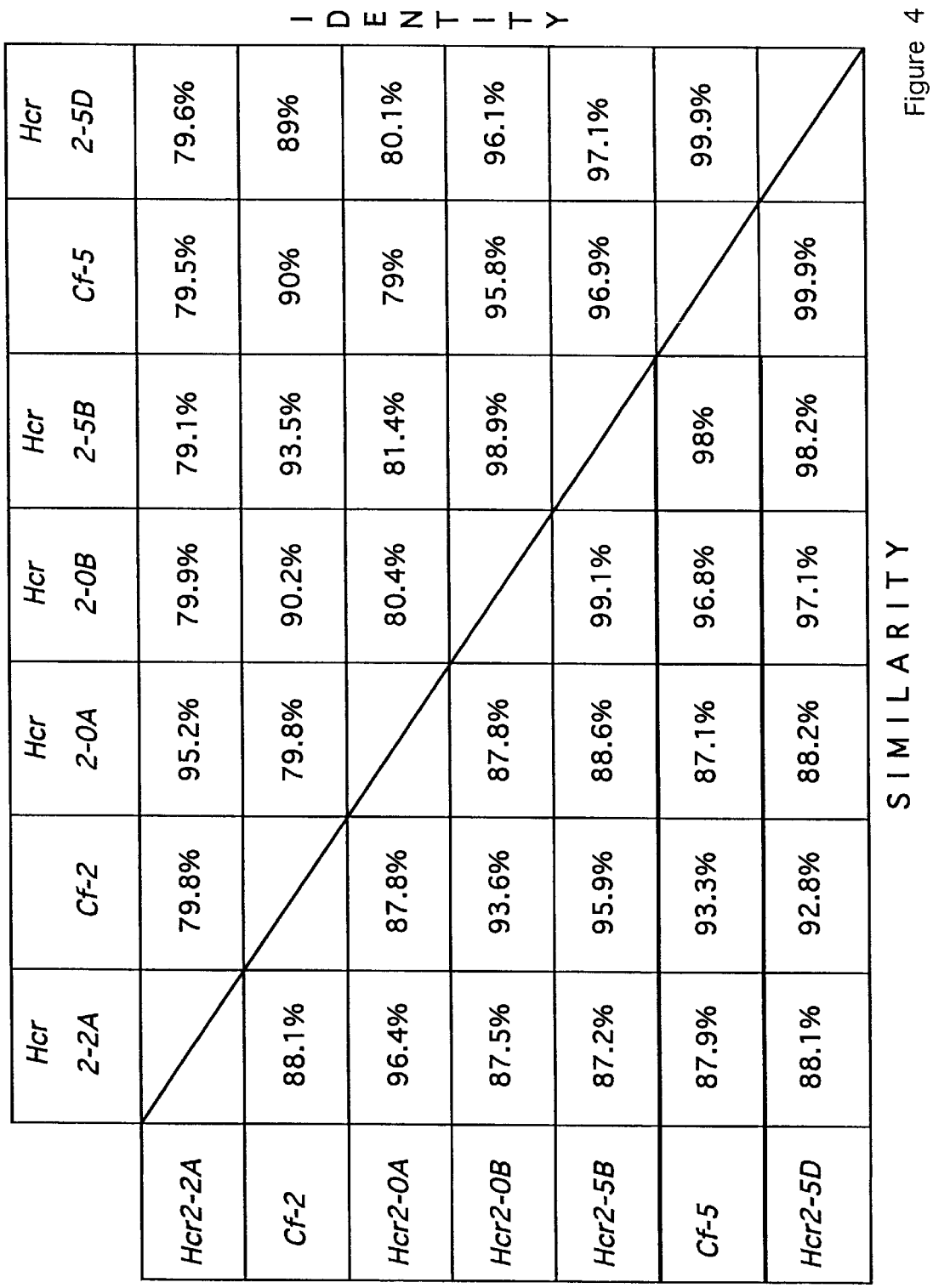
FIG. 4 shows the levels of similarity and identity between Cf-2, Cf-5 and several homologues. Analysis was performed using the standard program BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman.
Figure 9:
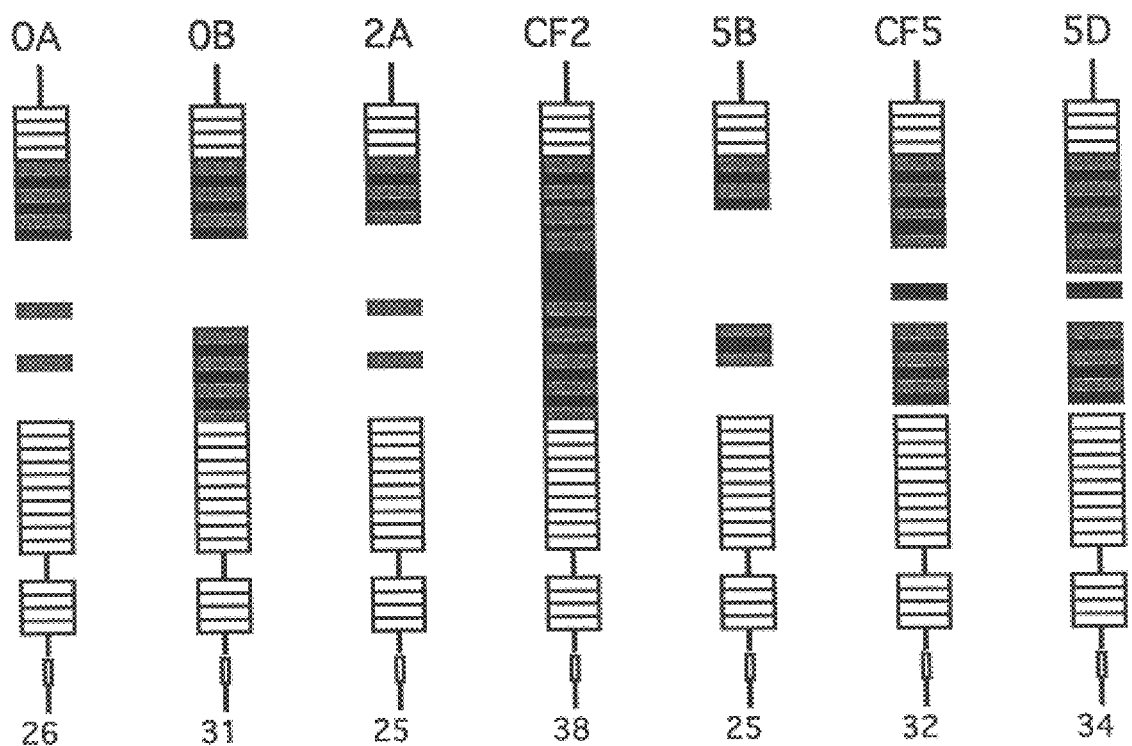
FIG. 9 shows a schematic representation of the proteins encoded by different Cf and Hcr genes of the Cf0, Cf2 and Cf5 loci of chromosome 6 of the tomato. Horizontal boxes represent individual LRRS, grey boxes indicate A-type repeats and black boxes indicated B-type repeats. Vertical boxes indicate the transmembrane domain. The number of LRRs in each encoded protein is shown beneath. All proteins are aligned to Cf2.

The Cf-5 resistance gene has been mapped to a similar chromosomal location to Cf-2 on tomato chromosome 6 (Dickinson et al., 1993; Jones et al. 1993). To more precisely determine the position of the Cf-5 gene, tomato crosses were set up to look for recombination between the Cf-2 and Cf-5 resistance genes. A plant that was heterozygous for both Cf-2 and Cf-5 was crossed to a *C. fulvum*-sensitive tomato line. Approximately 12,000 resulting F1 progeny were screened for resistance to *C. fulvum*, and a single sensitive plant was identified. DNA from this plant was analysed with the molecular markers including Cf-2 and other markers which map closely to the Cf-2 gene. The fact that only a single recombinant between Cf-2 and Cf-5 was obtained strongly suggested that these two resistance genes are indeed allelic or very closely linked. The molecular analysis of this plant also suggested that the Cf-5 gene may even be identified by the Cf-2 gene probe.

Isolation of binary cosmid vector clones that carry a genomic Cf-5 gene

To determine whether DNA identified by the molecular Cf-2 gene probe include the Cf-5 gene, DNA sequences were isolated from a plant that carried the Cf-5 gene and transformed into Cf-0 tomato plants.

A genomic DNA library was constructed from a stock that carried both the Cf▲4 gene on chromosome 1, and the Cf▲5 gene on chromosome 6. The library was constructed in a binary cosmid cloning vector pCLD04541, obtained from Dr C. Dean, John Innes Centre, Colney Lane, Norwich (see also Bent et al 1994). The library was randomly distributed into 144 pools containing about 1500 clones per pool, cells were grown from each pool and from 10 ml of cells, 9 ml were used for bulk plasmid DNA extractions, and 1 ml was used after addition of 0.2 ml of glycerol, to prepare a frozen stock. Plasmid DNA from the pools was isolated by alkaline lysis (Birnboim and Doly, 1979), and DNA samples were analyzed by hybridisation in "slot blots" and Southern blots with the molecular Cf-2 gene probe. Several pools proved positive in this assay.

For each pool, approximately 10,000 colonies were plated out and inspected for Cf-2 gene homology by colony hybridisation with a radioactive Cf-2 gene probe, and from each pool, single clones were isolated that carried such homology. These techniques are all well known to those skilled in the art.

These clones have been further characterized by Southern blot hybridisation using a Cf-2 gene probe, and by restriction enzyme mapping. These cosmids revealed four regions that hybridised to the Cf-2 gene probe. Subclones, each containing only a single region of homology, were generated in the same cosmid vector. These cosmids (Cosmid 8, KB2, KB3 and KB4) were subsequently used in plant transformation experiments, selecting for plant cells transformed to kanamycin resistance, using techniques well known to those skilled in the art. Transgenic tomato plants were produced (Fillati et al 1987; Horsch e al 1985) with at least one of each of the cosmids.

Assessment of cosmid function in transgenic tomato.

The function of a putative cloned Cf-5 gene has been assessed in transformed tomato by testing transformants for resistance to Avr5 carrying *C. fulvum*. Most transgenic plants containing cosmid KB2 were resistant to *C. fulvum* carrying Avr5. All transgenic plants containing the other cosmids were sensitive to *C. fulvum*. These data indicate that the genomic DNA which carries the Cf-5 gene is that piece which corresponds to the region labeled KB2. Thus the Cf-5 gene is the region identified by the Cf-2 gene probe and labelled KB2.

Of the cosmids which failed to confer resistance to *C. fulvum* carrying Avr5, cosmid 8 was shown to carry Hcr2-5B, KB3 was shown to carry Hcr2-5D and KB4 carries a region with only a small amount of similarity to any of the Hcr genes and which lacks any significant open reading frame.

Progeny of transgenic plants carrying KB2 were again tested for resistance to *C. fulvum* carrying Avr5 and were shown to segregate 3:1 resistant plants to susceptible plants. This is consistent with the gene contained in cosmid KB2 (Cf-5) being heritable in a Mendelian fashion. Progeny from plants carrying the other cosmids (Cosmids 8, KB3 and KB4) were all susceptible to *C. fulvum* carrying Avr5.

DNA sequence analysis of the Cf-5 gene

The DNA sequence of the 4 kb ClaI to BamHI region encompassing all of the Cf-2 hybridising region of KB2 has been determined, and is shown in FIG. 1 (SEQ ID NO:1 and SEQ ID NO:2).

The central core sequence carries a single major open reading frame which upon conceptual translation has revealed an interesting motif (the leucine rich repeat, or LRR) that can by hypothesised to be diagnostic of other resistance genes, as previously hypothesised for the Cf-9 gene. The open reading frame initiates with the translation start codon (ATG) at position 654 and finishes with the translation termination codon TAG at position 3558 with an intervening sequence that encodes a 968 amino acid polypeptide.

The amino acid sequence of the encoded polypeptide is shown in FIG. 2 (SEQ ID NO:3 and SEQ ID NO:4).

The DNA sequences of the regions encompassing all of the Cf-2 hybridising regions contained within Cosmid 8 and KB3 have been determined. Each sequence has a single major open reading frame which upon conceptual translation reveals encoded proteins with motifs characteristic of the Cf-5 resistance gene. The amino acid sequence encoded by the Cf-2 hybridising region of KB3 (also referred to as Hcr2-SD) shows very high homology to the CF-5 protein (FIG. 4). Specifically, Hcr2-5D contains 2 additional leucine rich repeats between amino acids 298 and 299 of CF-5 and a single amino acid corresponding to position 329 in CF-5 from a serine to an alanine.

Homologues of resistance genes Cf-2 and Cf-5, including Hcr2-5B and Hcr2-SD for which sequence information is provided herein, may be capable of and useful for conferring resistance when expressed in a plant, by a mechanism which does not involve recognition of Avr2 or Avr5 respectively.

REFERENCES

1. Ashfield T, et al., (1994) Mol.Plant.Mic.Int. 7:645–657.
2. Balint-Kurti P, et al., Theor.App.Genet. (1994) 88 pp 691–700.
3. Bent, A. F., et al., (1994) Science 265:1856.
4. Birnboim, H. C. and Doly, J. (1979) Nucl. Acids. Res. 7:1513–1520.
5. Chang C, et al., (1992) The Plant Cell 4:1263–1271.
6. De Wit, PJGM (1992) Ann.Rev.Phytopathol. 30:391–418.
7. Dickinson M, et al., (1993) Mol.Plant Mic.Int. 6:341–347.
8. Dixon M S, et al. (1995). High resolution mapping of the physical location of the Cf-2 gene. Mol.Plant.Mic.Int. 8:200–206.

9. Dixon M S, et al., (1996) Cell. 84:451–459.
10. Fillatti J J, et al. (1987). Bio/technol. 5:726–730.
11. Flor H H (1971). Ann.Rev.Phytopathol. 9:275–296.
12. Gabriel D W, et al. (1990). Ann. Rev. Phytopathol. 28:365–391.
13. Hammond-Kosack KE, et al. (1994) Mol. Plant.Mic.Int. 7: 58–70.
14. Hohn B. et al. (1980). Gene 11:291–298.
15. Horsch R B, et al. (1985). Science (Wash.). 227:1229–1231.
16. Johal G S, et al. (1992). Science (Wash.). 258:985–987.
17. Jones D A, et al. (1993). Mol.Plant Mic.Int. 6:348–357.
18. Jones J D G, et al. (1992). Transgen. Res. 1:285–297.
19. Jones D A, et al. (1994). Science (Wash. 266:789–793.
20. Keen N T (1992). Ann.Rev.Gen. 24:447–463.
21. Long S R (1993). Cell 73:921–935.
22. Martin G B, et al., (1993). Science 262:1432–1436.
23. Mindrinos M, et al., (1994). Cell 78:1089-1055.
24. Olszewski N E, et al. (1988). Nucl. Acids. Res 16:10765–10782.
25. Stein J C, et al. (1991). Proc.Natl.Acad.Sci.USA 88:8816–8820.
26. Thomas C M, et al (1994). Mol. & Gen.Genet. 242:573–585.
27. Valon C, et al (1993). Pl.Molec.Biol. 23:415–421.
28. van den Elzen P, et al. (1985). Plant. Mol. Biol. 5:149–154.
29. Walker J C (1993). Plant Journal 3:451–456.
30. Whitham S, et al. (1994). Cell 78:1011–1115.
31. Scofield , et al. (1996) Science 274:2063–2065.
32. Tang, et al. (1996) Science 274: 2060–2063.
33. Tigchelaar, EC (1984) Report of the Tomato Genetic Co-operative vol. 34, pp55–57.

What is claimed is:

1. An isolated polynucleotide which has a nucleotide sequence encoding a disease resistance polypeptide comprising an amino acid sequence selected from:
   (i) the amino acid sequence shown in FIG. 2A (SEQ ID NO:3); and
   (ii) the amino acid sequence shown in FIG. 2B (SEQ ID NO:4).

2. The polynucleotide according to claim 1 which has a nucleotide sequence encoding a polypeptide comprising the amino acid sequence shown in FIG. 2A (SEQ ID NO:3).

3. The polynucleotide according to claim 2 wherein said nucleotide sequence is as shown in FIG. 1A (SEQ ID NO:1).

4. The polynucleotide according to claim 1 which has a nucleotide sequence encoding a polypeptide comprising the amino acid sequence shown in FIG. 2B (SEQ ID NO:4).

5. The polynucleotide according to claim 4 wherein said nucleotide sequence is as shown in FIG. 1B (SEQ ID NO:2).

6. The polynucleotide according to claim 1 operably linked to a regulatory sequence for expression of said nucleotide sequence.

7. An isolated nucleic acid which comprises a nucleotide sequence complementary to at least 300 consecutive nucleotides of the polynucleotide of claim 1, wherein said nucleic acid inhibits expression of said polynucleotide in a plant cell.

8. The nucleic acid according to claim 7 operably linked to a regulatory sequence for transcription of said nucleic acid.

9. The nucleic acid according to claim 8 wherein the regulatory sequence comprises an inducible promoter.

10. A nucleic acid vector suitable for transformation of a host cell wherein said vector comprises the polynucleotide according to claim 1.

11. The nucleic acid vector according to claim 10 wherein said host cell is a plant cell.

12. A plant cell containing the polynucleotide according to claim 1, which polynucleotide is heterologous to said plant cell.

13. The plant cell according to claim 12 wherein said polynucleotide is incorporated within its genome.

14. A plant, a part thereof or a propagule thereof comprising the cell according to claim 12.

15. A method of producing a plant, the method comprising incorporating the polynucleotide according to claim 1 into a plant cell and regenerating a plant from said plant cell.

16. A method of producing a plant, the method comprising incorporating the nucleic acid according to claim 7 into a plant cell and regenerating a plant from said plant cell.

17. The method according to claim 15 further comprising sexually or asexually propagating a descendent plant from said plant, wherein said descendent plant comprises said polynucleotide.

18. The method according to claim 16 further comprising sexually or asexually propagating a descendent plant from said plant, wherein said descendent plant comprises said nucleic acid.

* * * * *

SEQUENCE LISTING

```
<160> NUMBER OF SEQ ID NOS: 10

<210> SEQ ID NO 1
<211> LENGTH: 3979
<212> TYPE: DNA
<213> ORGANISM: Lycopersicon esculentum

<400> SEQUENCE: 1
atcgatttta gagtcattgc aatttaattt tatcaaaata tttgagcatg aaaaatttga      60
aatggaggtg tcataaaaat aaaatacccct ttacaacacg actttattga gttgacgata    120
gttcaagtag ggaaaataaa taacttatta tttgaatata aaacttgcaa aaaaaaaaaa    180
gtgatattca aatttaattc tgaccattat ctcttgatat tctttgctct tcatttattt    240
gaatattcat ttttcaaaag ttccacatca taagacatca aatatcaagt aggtcccata    300
aaaataaaat accttctca acatgacaaa gaaagattga aaaatgacta acattttctc    360
aaagacaaaa acaaaacatg tgagagaaga gaattttgaa ccaaatgtat tatacactaa    420
gagtggtcat gatcattgtg tgataacaaa actattttgg caactttgac tcagtccttg    480
gctaaattag acctctaaca caacagtcca aaagttgact tgagaatgac aacattttct    540
tccctgatag caaccaaatt agcaaatttg gaaaaaacgt gtgtcttgtt gatctctaat    600
tagtataagt aacgtacaat atcctattga atcggaaaca ataaactcac actatgatga    660
tggttactag caaagtattc tcttcacttc agttttttcac tgttttctac ctctttacag    720
ttgcatttgc ttcgactgag gaggcaactg ccctcttgac atggaaagca actttcaaga    780
accagaataa ttccttttttg gcttcatgga cgacaagttc taatgcatgc aaggactggt    840
atggagttgt atgcttgaat ggtagggtaa acacgttgaa tattacaaat gccagtgtca    900
ttggtacact ttatgctttt ccattttcat ccctcccttt tctcgagaat cttgatctta    960
gcaacaacaa tatctctggt accattccac ctgagattgg taatctcaca aatcttgtct   1020
atcttgactt gaacaccaat cagatttcag gaacaattcc accacaaatc ggttcactag   1080
ccaagcttca gatcatccgc atatttaaca atcatttaaa tggctttatt cctgaagaaa   1140
taggttacct aaggtctctt actaagctat ctttgggtat caactttctt agtggttcta   1200
ttcctgcttc attgggcaat atgaccaact tgtcttttttt atttctttat gaaaatcagc   1260
tttctggctt tattcctgaa gaaataggtt acctaaggtc tcttactaag ctatctttgg   1320
atatcaactt tcttagtggt tccattcctg cttcattggg gaatctgaac aacttgtctt   1380
```

-continued

```
ttttgtatct ttacaataat cagctttctg gctctattcc tgaagaaata ggttacctaa     1440
ggtcacttac taagctatct ttgggtatca actttcttag tggttccatt cctgcttcat     1500 tgggaatct aaacaacttg tctaggttgg atctttacaa taataagctt tctggctcta      1560
ttcctgaaga aataggttac ctaaggtctc ttacttacct agatttgggt gagaatgctc     1620
ttaatggctc tattccttct tcattgggga atctaaacaa cttgtctagg ttggatcttt    1680
acaataataa gctttctggc tctattcctg aagaaatagg ttacctaagg tctcttactt    1740
acctagattt gggtgagaat gctcttaatg gctctattcc tgcttcattg gggaatctga    1800
acaacttgtt tatgttgtat ctttacaata tcagctttc tggctctatt cctgaagaaa     1860
taggttacct gagttctctt actgaactat atttgggtaa taactctctt aatggctcta    1920
ttcctgcttc attggggaat ctgaacaact tgtttatgtt gtatctttac aataatcagc    1980
tttctggctc tattcctgaa gaaataggtt acctgagttc tcttactgaa ctattttgg     2040 gtaataactc tcttaatggc tctattcctg cttcattggg gaatctaaac aacttgtcta    2100
ggttgtatct ttacaataat cagctttctg gctctattcc tgcttcattt ggcaatatga    2160
gaaatctgca aactctgttt ctcagtgata acgatctcat tggggaaatt ccttcatttg    2220
tgtgcaattt gacatcactg gaagtgttgt atatgtcgag aaacaatttg aagggaaaag    2280
ttccgcaatg tttgggtaat atcagtgacc ttcacatttt gtcgatgtca tctaatagtt    2340
tcagaggaga gctcccttca tctatttcca atttaacatc actaaaaata cttgattttg    2400
gcagaaacaa tctggaggga gcaataccac aattttttgg caatattagt agcctccagg    2460
tttttgatat gcagaataac aaactttctg ggactcttcc aacaaatttt agcattggat    2520
gttcactgat aagtctcaac ttgcatggca atgaactagc agatgaaatc cctcggtctt    2580
tggacaattg caaaaagctg caagttcttg atttaggaga caatcaactc aacgacacat    2640
ttcccatgtg gttgggaact tgccagagc tgagagtttt aaggttgaca tcgaataaat      2700
tgcatggacc tataagatca tcaggggctg aaatcatgtt tcctgatctc cgaatcatag     2760
atctctctcg caatgcattc tcgcaagact taccaacgag tctatttgaa catttgaaag    2820
ggatgaggac agttgataaa acaatggagg aaccaagtta tgaaagctat tacgatgact    2880
cggtggtagt tgtgacaaag ggattggagc ttgaaattgt gagaattctg tctttgtaca    2940
caattatcga tctttcaagc aacaaatttg aaggacatat tccttctgtc ctgggagatc    3000
tcattgcgat ccgtgtactt aatgtatctc ataatgcatt gcaaggctat ataccatcat    3060
cacttggaag tttatctata ctggaatcac tagacctttc gtttaaccaa ctttcgggag    3120
agataccaca caacttgct tctcttacgt ttcttgaagt cttaaatctc tcccacaatt      3180
atctccaagg atgcatccct caaggacctc aattccgtac ctttgagagc aattcatatg    3240
aaggtaatga tggattacgt ggatatccag tttcaaaagg ttgtggcaaa gatcctgtgt    3300
cagagaaaaa ctatacagtg tctgcgctag aagatcaaga aagcaattct gaattttttca    3360 atgattttg gaaagcagct ctgatgggct atggaagtgg actgtgtatt ggcatatcca    3420
taatatatat cttgatctcg actggaaatc taagatggct tgcaagaatc attgaagaac    3480
tggaacacaa aattatcgtg caaggagaa agaagcagcg aggtcaaaga aattacagaa    3540
gaagaaataa tcgcttctag acaagttacc aatacagaaa gatttgattt cagaacttca    3600
ggtattcaag ctaacctcta acacttatct tttttagttt attctaacaa ctaatatatg    3660
tttttttttt tatcaacaaa tacttattaa cgcttgagac aaattgctag taatcagttg    3720
```

```
gaagttgtga tatataacaa aggctaaaaa tttatagttg tgtgactcac tttcttattt      3780
ttccagattt tcaggagcca agaataagaa gacgctggtg taaaggattt gcttcttcct      3840
gtgttgcagc ttatgatgtt ggattagatt tttagtttta taagcttttc ttcagttggg      3900
aaaatgtaat attatgaatt tgatgatat acaataaatg ttgtgtttat tgaatgatat       3960
gtatgcattt atcggatcc                                                   3979

<210> SEQ ID NO 2
<211> LENGTH: 3979
<212> TYPE: DNA
<213> ORGANISM: Lycopersicon esculentum

<400> SEQUENCE: 2
atcgatttta gagtcattgc aatttaattt tatcaaaata tttgagcatg aaaaatttga        60
aatggaggtg tcataaaaat aaaatacccT ttacaacacg actttattga gttgacgata       120
gttcaagtag ggaaaataaa taacttatta tttgaatata aaacttgcaa aaaaaaaaa        180 gtgatattca aatttaattc tgaccattat ctcttgatat tctttgctct tcatttattt      240
gaatattcat ttttcaaaag ttccacatca taagacatca aatatcaagt aggtcccata      300
aaaataaaat acccttctca acatgacaaa gaaagattga aaaatgacta acattttctc      360
aaagacaaaa acaaaacatg tgagagaaga gaattttgaa ccaaatgtat tatacactaa      420
gagtggtcat gatcattgtg tgataacaaa actattttgg caactttgac tcagtccttg      480
gctaaattag acctctaaca caacagtcca aaagttgact tgagaatgac aacattttct      540
tccctgatag caaccaaatt agcaaatttg gaaaaaacgt gtgtcttgtt gatctctaat      600
tagtataagt aacgtacaat atcctattga atcggaaaca ataaactcac actatgatga      660
tggttactag caaagtattc tcttcacttc agttttctcac tgttttctac ctctttacag     720
ttgcatttgc ttcgactgag gaggcaactg ccctcttgaa atggaaagca actttcaaga      780
accagaataa ttcctttttg gcttcatgga cgacaagttc taatgcatgc aaggactggt      840
atggagttgt atgcttgaat ggtagggtaa acacgttgaa tattacaaat gccagtgtca      900
ttggtacact ttatgctttt ccattttcat ccctcccttt tctcgagaat cttgatctta      960
gcaacaacaa tatctctggt accattccac ctgagattgg taatctcaca aatcttgtct     1020
atcttgactt gaacaccaat cagatttcag gaacaattcc accacaaatc ggttcactag     1080
ccaagcttca gatcatccgc atatttaaca atcatttaaa tggctttatt cctgaagaaa     1140
taggttacct aaggtctctt actaagctat ctttgggtat caactttctt agtggttcta     1200
ttcctgcttc attgggcaat atgaccaact tgtctttttt atttctttat gaaaatcagc     1260
tttctggctt tattcctgaa gaaataggtt acctaaggtc tcttactaag ctatctttgg     1320
atatcaactt tcttagtggt tccattcctg cttcattggg gaatctgaac aacttgtctt     1380
ttttgtatct ttacaataat cagctttctg gctctattcc tgaagaaata ggttacctaa     1440
ggtcacttac taagctatct ttgggtatca acttcttag tggttccatt cctgcttcat      1500
tgggaatctc aaacaacttg tctaggttgg atcttacaa taataagctt tctggctcta     1560
ttcctgaaga aataggttac ctaaggtctc ttacttacct agatttgggt gagaatgctc     1620
ttaatggctc tattccttct tcattgggga atctaaacaa cttgtctagg ttggatcttt     1680
acaataataa gctttctggc tctattcctg aagaaatagg ttacctaagg tctcttactt     1740
acctagattt gggtgagaat gctcttaatg gctctattcc tgcttcattg gggaatctga     1800
acaacttgtt tatgttgtat ctttacaata atcagctttc tggctctatt cctgaagaaa     1860
```

-continued

```
taggttacct gagttctctt actgaactat atttgggtaa taactctctt aatggctcta      1920
ttcctgcttc attggggaat ctgaacaact tgtttatgtt gtatctttac aataatcagc      1980
tttctggctc tattcctgaa gaaataggtt acctgagttc tcttactgaa ctattttcgg      2040
gtaataactc tcttaatggc tctattcctg cttcattggg gaatctaaac aacttgtcta      2100
ggttgtatct ttacaataat cagctttctg gctctattcc tgcttcattt ggcaatatga     2160
gaaatctgca aactctgttt ctcagtgata acgatctcat tggggaaatt ccttcatttg     2220
tgtgcaattt gacatcactg gaagtgttgt atatgtcgag aaacaatttg aagggaaaag     2280
ttccgcaatg tttgggtaat atcagtgacc ttcacatttt gtcgatgtca tctaatagtt     2340
tcagaggaga gctcccttca tctatttcca atttaacatc actaaaaata cttgattttg     2400
gcagaaacaa tctggaggga gcaataccac aatttttttgg caatattagt agcctccagg    2460
tttttgatat gcagaataac aaactttctg ggactcttcc aacaaatttt agcattggat     2520
gttcactgat aagtctcaac ttgcatggca atgaactagc agatgaaatc cctcggtctt     2580
tggacaattg caaaaagctg caagttcttg atttaggaga caatcaactc aacgacacat     2640
ttcccatgtg gttgggaact ttgccagagc tgagagtttt aaggttgaca tcgaataaat     2700
tgcatggacc tataagatca tcaggggctg aaatcatgtt tcctgatctc cgaatcatag     2760
atctctctcg caatgcattc tcgcaagact taccaacgag tctatttgaa catttgaaag     2820
ggatgaggac agttgataaa acaatggagg aaccaagtta tgaaagctat tacgatgact     2880
cggtggtagt tgtgacaaag ggattggagc ttgaaattgt gagaattctg tctttgtaca     2940
caattatcga tctttcaagc aacaaatttg aaggacatat tccttctgtc ctgggagatc     3000
tcattgcgat ccgtgtactt aatgtatctc ataatgcatt gcaaggctat ataccatcat     3060
cacttggaag tttatctata ctggaatcac tagacctttc gtttaaccaa cttttcgggag    3120 agataccaca acaacttgct tctcttacgt ttcttgaagt cttaaatctc tcccacaatt     3180
atctccaagg atgcatccct caaggacctc aattccgtac cttttgagagc aattcatatg    3240 aaggtaatga tggattacgt ggatatccag tttcaaaagg ttgtggcaaa gatcctgtgt    3300
cagagaaaaa ctatacagtg tctgcgctag aagatcaaga aagcaattct gaattttttca   3360 atgattttttg gaaagcagct ctgatgggct atggaagtgg actgtgtatt ggcatatcca   3420
taatatatat cttgatctcg actgaaaatc taagatggct tgcaagaatc attgaagaac    3480
tggaacacaa aattatcgtg caaaggagaa agaagcagcg aggtcaaaga aattacagaa    3540
gaagaaataa tcgcttctag acaagttacc aatacagaaa gatttgattt cagaacttca    3600
ggtattcaag ctaacctcta acacttatct tttttagttt attctaacaa ctaatatatg     3660
tttttttttt tatcaacaaa tacttattaa cgcttgagac aaattgctag taatcagttg    3720
gaagttgtga tatataacaa aggctaaaaa tttatagttg tgtgactcac tttcttattt    3780
ttccagattt tcaggagcca agaataagaa gacgctggtg taaaggattt gcttcttcct    3840
gtgttgcagc ttatgatgtt ggattagatt tttagttttta taagcttttc ttcagttggg   3900
aaaatgtaat attatgaatt ttgatgatat acaataaatg ttgtgtttat tgaatgatat    3960
gtatgcattt atcggatcc                                                  3979
```

<210> SEQ ID NO 3
<211> LENGTH: 968
<212> TYPE: PRT
<213> ORGANISM: Lycopersicon esculentum -continued

<400> SEQUENCE: 3

```
Met Met Met Val Thr Ser Lys Val Phe Ser Ser Leu Gln Phe Phe Thr
 1               5                  10                  15

Val Phe Tyr Leu Phe Thr Val Ala Phe Ala Ser Thr Glu Glu Ala Thr
             20                  25                  30

Ala Leu Leu Thr Trp Lys Ala Thr Phe Lys Asn Gln Asn Asn Ser Phe
             35                  40                  45

Leu Ala Ser Trp Thr Thr Ser Ser Asn Ala Cys Lys Asp Trp Tyr Gly
         50                  55                  60

Val Val Cys Leu Asn Gly Arg Val Asn Thr Leu Asn Ile Thr Asn Ala
 65                  70                  75                  80

Ser Val Ile Gly Thr Leu Tyr Ala Phe Pro Phe Ser Ser Leu Pro Phe
                 85                  90                  95

Leu Glu Asn Leu Asp Leu Ser Asn Asn Asn Ile Ser Gly Thr Ile Pro
                100                 105                 110

Pro Glu Ile Gly Asn Leu Thr Asn Leu Val Tyr Leu Asp Leu Asn Thr
            115                 120                 125

Asn Gln Ile Ser Gly Thr Ile Pro Pro Gln Ile Gly Ser Leu Ala Lys
    130                 135                 140

Leu Gln Ile Ile Arg Ile Phe Asn Asn His Leu Asn Gly Phe Ile Pro
145                 150                 155                 160

Glu Glu Ile Gly Tyr Leu Arg Ser Leu Thr Lys Leu Ser Leu Gly Ile
                165                 170                 175

Asn Phe Leu Ser Gly Ser Ile Pro Ala Ser Leu Gly Asn Met Thr Asn
            180                 185                 190

Leu Ser Phe Leu Phe Leu Tyr Glu Asn Gln Leu Ser Gly Phe Ile Pro
        195                 200                 205

Glu Glu Ile Gly Tyr Leu Arg Ser Leu Thr Lys Leu Ser Leu Asp Ile
    210                 215                 220

Asn Phe Leu Ser Gly Ser Ile Pro Ala Ser Leu Gly Asn Leu Asn Asn
225                 230                 235                 240

Leu Ser Phe Leu Tyr Leu Tyr Asn Asn Gln Leu Ser Gly Ser Ile Pro
                245                 250                 255

Glu Glu Ile Gly Tyr Leu Arg Ser Leu Thr Lys Leu Ser Leu Gly Ile
            260                 265                 270

Asn Phe Leu Ser Gly Ser Ile Pro Ala Ser Leu Gly Asn Leu Asn Asn
        275                 280                 285

Leu Ser Arg Leu Asp Leu Tyr Asn Asn Lys Leu Ser Gly Ser Ile Pro
    290                 295                 300

Glu Glu Ile Gly Tyr Leu Arg Ser Leu Thr Tyr Leu Asp Leu Gly Glu
305                 310                 315                 320

Asn Ala Leu Asn Gly Ser Ile Pro Ser Ser Leu Gly Asn Leu Asn Asn
                325                 330                 335

Leu Ser Arg Leu Asp Leu Tyr Asn Asn Lys Leu Ser Gly Ser Ile Pro
            340                 345                 350

Glu Glu Ile Gly Tyr Leu Arg Ser Leu Thr Tyr Leu Asp Leu Gly Glu
        355                 360                 365

Asn Ala Leu Asn Gly Ser Ile Pro Ala Ser Leu Gly Asn Leu Asn Asn
    370                 375                 380

Leu Phe Met Leu Tyr Leu Tyr Asn Asn Gln Leu Ser Gly Ser Ile Pro
385                 390                 395                 400

Glu Glu Ile Gly Tyr Leu Ser Ser Leu Thr Glu Leu Tyr Leu Gly Asn
                405                 410                 415
```

```
Asn Ser Leu Asn Gly Ser Ile Pro Ala Ser Leu Gly Asn Leu Asn Asn
            420                 425                 430

Leu Phe Met Leu Tyr Leu Tyr Asn Asn Gln Leu Ser Gly Ser Ile Pro
            435                 440                 445

Glu Glu Ile Gly Tyr Leu Ser Ser Leu Thr Glu Leu Phe Leu Gly Asn
            450                 455                 460

Asn Ser Leu Asn Gly Ser Ile Pro Ala Ser Leu Gly Asn Leu Asn Asn
465                 470                 475                 480

Leu Ser Arg Leu Tyr Leu Tyr Asn Asn Gln Leu Ser Gly Ser Ile Pro
                485                 490                 495

Ala Ser Phe Gly Asn Met Arg Asn Leu Gln Thr Leu Phe Leu Ser Asp
                500                 505                 510

Asn Asp Leu Ile Gly Glu Ile Pro Ser Phe Val Cys Asn Leu Thr Ser
            515                 520                 525

Leu Glu Val Leu Tyr Met Ser Arg Asn Asn Leu Lys Gly Lys Val Pro
            530                 535                 540

Gln Cys Leu Gly Asn Ile Ser Asp Leu His Ile Leu Ser Met Ser Ser
545                 550                 555                 560

Asn Ser Phe Arg Gly Glu Leu Pro Ser Ser Ile Ser Asn Leu Thr Ser
                565                 570                 575

Leu Lys Ile Leu Asp Phe Gly Arg Asn Asn Leu Glu Gly Ala Ile Pro
                580                 585                 590

Gln Phe Phe Gly Asn Ile Ser Ser Leu Gln Val Phe Asp Met Gln Asn
            595                 600                 605

Asn Lys Leu Ser Gly Thr Leu Pro Thr Asn Phe Ser Ile Gly Cys Ser
            610                 615                 620

Leu Ile Ser Leu Asn Leu His Gly Asn Glu Leu Ala Asp Glu Ile Pro
625                 630                 635                 640

Arg Ser Leu Asp Asn Cys Lys Lys Leu Gln Val Leu Asp Leu Gly Asp
                645                 650                 655

Asn Gln Leu Asn Asp Thr Phe Pro Met Trp Leu Gly Thr Leu Pro Glu
            660                 665                 670

Leu Arg Val Leu Arg Leu Thr Ser Asn Lys Leu His Gly Pro Ile Arg
            675                 680                 685

Ser Ser Gly Ala Glu Ile Met Phe Pro Asp Leu Arg Ile Ile Asp Leu
            690                 695                 700

Ser Arg Asn Ala Phe Ser Gln Asp Leu Pro Thr Ser Leu Phe Glu His
705                 710                 715                 720

Leu Lys Gly Met Arg Thr Val Asp Lys Thr Met Glu Glu Pro Ser Tyr
                725                 730                 735

Glu Ser Tyr Tyr Asp Asp Ser Val Val Val Thr Lys Gly Leu Glu
                740                 745                 750

Leu Glu Ile Val Arg Ile Leu Ser Leu Tyr Thr Ile Ile Asp Leu Ser
            755                 760                 765

Ser Asn Lys Phe Glu Gly His Ile Pro Ser Val Leu Gly Asp Leu Ile
            770                 775                 780

Ala Ile Arg Val Leu Asn Val Ser His Asn Ala Leu Gln Gly Tyr Ile
785                 790                 795                 800

Pro Ser Ser Leu Gly Ser Leu Ser Ile Leu Glu Ser Leu Asp Leu Ser
                805                 810                 815

Phe Asn Gln Leu Ser Gly Glu Ile Pro Gln Gln Leu Ala Ser Leu Thr
            820                 825                 830
```

```
Phe Leu Glu Val Leu Asn Leu Ser His Asn Tyr Leu Gln Gly Cys Ile
            835                 840                 845

Pro Gln Gly Pro Gln Phe Arg Thr Phe Glu Ser Asn Ser Tyr Glu Gly
        850                 855                 860

Asn Asp Gly Leu Arg Gly Tyr Pro Val Ser Lys Gly Cys Gly Lys Asp
865                 870                 875                 880

Pro Val Ser Glu Lys Asn Tyr Thr Val Ser Ala Leu Glu Asp Gln Glu
            885                 890                 895

Ser Asn Ser Glu Phe Phe Asn Asp Phe Trp Lys Ala Ala Leu Met Gly
            900                 905                 910

Tyr Gly Ser Gly Leu Cys Ile Gly Ile Ser Ile Ile Tyr Ile Leu Ile
            915                 920                 925

Ser Thr Gly Asn Leu Arg Trp Leu Ala Arg Ile Ile Glu Glu Leu Glu
            930                 935                 940

His Lys Ile Ile Val Gln Arg Lys Lys Gln Arg Gly Gln Arg Asn
945                 950                 955                 960

Tyr Arg Arg Arg Asn Asn Arg Phe
                965

<210> SEQ ID NO 4
<211> LENGTH: 968
<212> TYPE: PRT
<213> ORGANISM: Lycopersicon esculentum

<400> SEQUENCE: 4

Met Met Met Val Thr Ser Lys Val Phe Ser Ser Leu Gln Phe Phe Thr
 1               5                  10                  15

Val Phe Tyr Leu Phe Thr Val Ala Phe Ala Ser Thr Glu Glu Ala Thr
            20                  25                  30

Ala Leu Leu Lys Trp Lys Ala Thr Phe Lys Asn Gln Asn Asn Ser Phe
        35                  40                  45

Leu Ala Ser Trp Thr Thr Ser Ser Asn Ala Cys Lys Asp Trp Tyr Gly
    50                  55                  60

Val Val Cys Leu Asn Gly Arg Val Asn Thr Leu Asn Ile Thr Asn Ala
65                  70                  75                  80

Ser Val Ile Gly Thr Leu Tyr Ala Phe Pro Phe Ser Ser Leu Pro Phe
                85                  90                  95

Leu Glu Asn Leu Asp Leu Ser Asn Asn Asn Ile Ser Gly Thr Ile Pro
            100                 105                 110

Pro Glu Ile Gly Asn Leu Thr Asn Leu Val Tyr Leu Asp Leu Asn Thr
        115                 120                 125

Asn Gln Ile Ser Gly Thr Ile Pro Pro Gln Ile Gly Ser Leu Ala Lys
    130                 135                 140

Leu Gln Ile Ile Arg Ile Phe Asn Asn His Leu Asn Gly Phe Ile Pro
145                 150                 155                 160

Glu Glu Ile Gly Tyr Leu Arg Ser Leu Thr Lys Leu Ser Leu Gly Ile
                165                 170                 175

Asn Phe Leu Ser Gly Ser Ile Pro Ala Ser Leu Gly Asn Met Thr Asn
            180                 185                 190

Leu Ser Phe Leu Phe Leu Tyr Glu Asn Gln Leu Ser Gly Phe Ile Pro
        195                 200                 205

Glu Glu Ile Gly Tyr Leu Arg Ser Leu Thr Lys Leu Ser Leu Asp Ile
    210                 215                 220

Asn Phe Leu Ser Gly Ser Ile Pro Ala Ser Leu Gly Asn Leu Asn Asn
225                 230                 235                 240
```

-continued

```
Leu Ser Phe Leu Tyr Leu Tyr Asn Asn Gln Leu Ser Gly Ser Ile Pro
                245                 250                 255

Glu Glu Ile Gly Tyr Leu Arg Ser Leu Thr Lys Leu Ser Leu Gly Ile
                260                 265                 270

Asn Phe Leu Ser Gly Ser Ile Pro Ala Ser Leu Gly Asn Leu Asn Asn
                275                 280                 285

Leu Ser Arg Leu Asp Leu Tyr Asn Asn Lys Leu Ser Gly Ser Ile Pro
                290                 295                 300

Glu Glu Ile Gly Tyr Leu Arg Ser Leu Thr Tyr Leu Asp Leu Gly Glu
305                 310                 315                 320

Asn Ala Leu Asn Gly Ser Ile Pro Ser Ser Leu Gly Asn Leu Asn Asn
                325                 330                 335

Leu Ser Arg Leu Asp Leu Tyr Asn Asn Lys Leu Ser Gly Ser Ile Pro
                340                 345                 350

Glu Glu Ile Gly Tyr Leu Arg Ser Leu Thr Tyr Leu Asp Leu Gly Glu
                355                 360                 365

Asn Ala Leu Asn Gly Ser Ile Pro Ala Ser Leu Gly Asn Leu Asn Asn
                370                 375                 380

Leu Phe Met Leu Tyr Leu Tyr Asn Asn Gln Leu Ser Gly Ser Ile Pro
385                 390                 395                 400

Glu Glu Ile Gly Tyr Leu Ser Ser Leu Thr Glu Leu Tyr Leu Gly Asn
                405                 410                 415

Asn Ser Leu Asn Gly Ser Ile Pro Ala Ser Leu Gly Asn Leu Asn Asn
                420                 425                 430

Leu Phe Met Leu Tyr Leu Tyr Asn Asn Gln Leu Ser Gly Ser Ile Pro
                435                 440                 445

Glu Glu Ile Gly Tyr Leu Ser Ser Leu Thr Glu Leu Phe Leu Gly Asn
                450                 455                 460

Asn Ser Leu Asn Gly Ser Ile Pro Ala Ser Leu Gly Asn Leu Asn Asn
465                 470                 475                 480

Leu Ser Arg Leu Tyr Leu Tyr Asn Asn Gln Leu Ser Gly Ser Ile Pro
                485                 490                 495

Ala Ser Phe Gly Asn Met Arg Asn Leu Gln Thr Leu Phe Leu Ser Asp
                500                 505                 510

Asn Asp Leu Ile Gly Glu Ile Pro Ser Phe Val Cys Asn Leu Thr Ser
                515                 520                 525

Leu Glu Val Leu Tyr Met Ser Arg Asn Asn Leu Lys Gly Lys Val Pro
                530                 535                 540

Gln Cys Leu Gly Asn Ile Ser Asp Leu His Ile Leu Ser Met Ser Ser
545                 550                 555                 560

Asn Ser Phe Arg Gly Glu Leu Pro Ser Ser Ile Ser Asn Leu Thr Ser
                565                 570                 575

Leu Lys Ile Leu Asp Phe Gly Arg Asn Asn Leu Glu Gly Ala Ile Pro
                580                 585                 590

Gln Phe Phe Gly Asn Ile Ser Ser Leu Gln Val Phe Asp Met Gln Asn
                595                 600                 605

Asn Lys Leu Ser Gly Thr Leu Pro Thr Asn Phe Ser Ile Gly Cys Ser
                610                 615                 620

Leu Ile Ser Leu Asn Leu His Gly Asn Glu Leu Ala Asp Glu Ile Pro
625                 630                 635                 640

Arg Ser Leu Asp Asn Cys Lys Lys Leu Gln Val Leu Asp Leu Gly Asp
                645                 650                 655
```

-continued

```
Asn Gln Leu Asn Asp Thr Phe Pro Met Trp Leu Gly Thr Leu Pro Glu
            660                 665                 670
Leu Arg Val Leu Arg Leu Thr Ser Asn Lys Leu His Gly Pro Ile Arg
            675                 680                 685
Ser Ser Gly Ala Glu Ile Met Phe Pro Asp Leu Arg Ile Ile Asp Leu
            690                 695                 700
Ser Arg Asn Ala Phe Ser Gln Asp Leu Pro Thr Ser Leu Phe Glu His
705                 710                 715                 720
Leu Lys Gly Met Arg Thr Val Asp Lys Thr Met Glu Glu Pro Ser Tyr
                725                 730                 735
Glu Ser Tyr Tyr Asp Asp Ser Val Val Val Thr Lys Gly Leu Glu
            740                 745                 750
Leu Glu Ile Val Arg Ile Leu Ser Leu Tyr Thr Ile Ile Asp Leu Ser
            755                 760                 765
Ser Asn Lys Phe Glu Gly His Ile Pro Ser Val Leu Gly Asp Leu Ile
            770                 775                 780
Ala Ile Arg Val Leu Asn Val Ser His Asn Ala Leu Gln Gly Tyr Ile
785                 790                 795                 800
Pro Ser Ser Leu Gly Ser Leu Ser Ile Leu Glu Ser Leu Asp Leu Ser
                805                 810                 815
Phe Asn Gln Leu Ser Gly Glu Ile Pro Gln Gln Leu Ala Ser Leu Thr
            820                 825                 830
Phe Leu Glu Val Leu Asn Leu Ser His Asn Tyr Leu Gln Gly Cys Ile
            835                 840                 845
Pro Gln Gly Pro Gln Phe Arg Thr Phe Glu Ser Asn Ser Tyr Glu Gly
            850                 855                 860
Asn Asp Gly Leu Arg Gly Tyr Pro Val Ser Lys Gly Cys Gly Lys Asp
865                 870                 875                 880
Pro Val Ser Glu Lys Asn Tyr Thr Val Ser Ala Leu Glu Asp Gln Glu
                885                 890                 895
Ser Asn Ser Glu Phe Phe Asn Asp Phe Trp Lys Ala Ala Leu Met Gly
            900                 905                 910
Tyr Gly Ser Gly Leu Cys Ile Gly Ile Ser Ile Ile Tyr Ile Leu Ile
            915                 920                 925
Ser Thr Gly Asn Leu Arg Trp Leu Ala Arg Ile Ile Glu Glu Leu Glu
            930                 935                 940
His Lys Ile Ile Val Gln Arg Lys Lys Gln Arg Gly Gln Arg Asn
945                 950                 955                 960
Tyr Arg Arg Arg Asn Asn Arg Phe
                965
```

<210> SEQ ID NO 5
<211> LENGTH: 3541
<212> TYPE: DNA
<213> ORGANISM: Lycopersicon esculentum

<400> SEQUENCE: 5

```
aaaatttgaa atggaggtgt cataaaaata aaataccctt tacaacacga ctttattgag     60
ttgacgatag ttcaagtagg gaaataaaat aacttattat ttgaatataa aacttgcaaa    120
aaaaaaaaag tgatattcaa atttaattct gaccattatc tcttgatatt ctttgctctt    180
catttatttg aatattcatt tttcaaaagt tccacatcat aagacatcaa atatcaagta    240
ggtcccataa aataaaata cccttctcaa catgacaaag aaagattgaa aaatgactaa    300
catttctca aagacaaaaa caaacatgt gagagaagag aattttgaac caaatgtatt    360
```

-continued

```
atacactaag agtggtcatg atcattgtgt gataacaaaa ctattttggc aactttgact       420
cagtccttgg ctaaattaga cctctaacac aacagtccaa aagttgactt gagaatgaca       480
acatttctt ccctgatagc aaccaaatta gcaaatttgg aaaaaacgtg tgtcttgttg       540
atctttaatt agtataagtt acgtacaata tcctattgaa tcggaaacaa taaactcaaa       600
ctatgatgat ggttactagc aaagtattct cttcacttca gtttttcact gttttctacc       660
tctttacagt tgcatttgct tcgactgagg aggcaactgc cctcttgaaa tggaaagcaa       720
cttcaagaa ccagaataat tccttttttgg cttcatggac acaagttct aatgcatgca        780
aggactggta tggagttgta tgcttgaatg gtagggtaaa cacgttgaat attacaaatg       840
ccagtgtcat tggtacactt tatgcttttc cattttcatc cctccctttt ctcgagaatc       900
ttgatcttag caacaacaat atctctggta ccattccacc tgagattggt aatctcacaa       960
atcttgtcta tcttgacttg aacaccaatc agatttcagg aacaattcca ccacaaatcg      1020
gttcactagc caagcttcag atcatccgca tatttaacaa tcatttaaat ggctttattc      1080
ctgaagaaat aggttaccta aggtctctta ctaagctatc tttgggtatc aactttctta      1140
gtggttctat tcctgcttca ttgggcaata tgaccaactt gtcttttttta tttctttatg    1200
aaaatcagct ttctggctttt attcctgaag aaataggtta cctaaggtct cttactaagc    1260
tatctttgga tatcaacttt cttagtggtt ccattcctgc ttcattgggg aatctgaaca      1320
acttgtcttt tttgtatctt tacaataatc agctttctgg ctctattcct gaagaaatag     1380
gttacctaag gtctcttact tacctagatt tgaaagagaa tgctcttaat ggctctattc     1440
ctgcttcatt ggggaatctg aacaacttgt ctaggttgta tctttacaat aatcagctttt    1500
ctggctctat tcctgaagaa ataggttact tgagttctct tactaatcta tatttgggta     1560
ataactctct tattggactt attcctgctt cattcggcaa tatgagaaat ctgcaagctc      1620
tgtttctcaa tgataacaat ctcattgggg aaattccttc atttgtgtgc aatttaacat     1680
cactagaact gttgtatatg ccgagaaaca atttgaaggg aaaagttccg caatgtttgg     1740
gtaatatcag tgaccttctg gttttgtcaa tgtcatctaa tagtttcagt ggagagctcc    1800
cttcatctat ttccaattta acatcactaa aaatacttga ttttggcaga acaatctgg     1860
agggagcaat accacaatgt tttggcaata ttagtagcct ccaggttttt gatatgcaga    1920
ataacaaact ttctgggact cttccaacaa atttttagcat tggatgttca ctgataagtc    1980
tcaacttgca tggcaatgaa ctagaggatg aaatcccttg gtctttggac aattgcaaaa    2040
agctgcaagt tcttgattta ggagacaatc aactcaacga cacatttccc atgtggttgg    2100
gaactttgcc agagctgaga gttttaaggt tgacatcgaa taaattgcat ggacctataa    2160
gatcatcagg ggctgaaatc atgtttcctg atcttcgaat catagatctc tctcgcaatg    2220
cattctcgca agacttacca acaagtctat ttgaacattt gaaagggatg aggacagttg    2280
ataaaacaat ggaggaacca agctatgaaa tatattacga ttcggttgta gttgtgacaa    2340
agggattgga gcttgaaatt gtgagaattc tgtctttgta cacagttatc gatctttcaa    2400
gcaacaaatt tgaaggacat attccttctg tcctgggaga tctcattgcg atccgtgtac    2460
ttaatgtatc tcataatgca ttgcaaggct ataccatc atcacttgga agtttatcta      2520
tactggaatc actagacctt tcgtttaacc aactttcggg agagatacca caacaacttg    2580
cttctcttac gttccttgaa ttcttaaatc tctcccacaa ttatctccaa ggatgcatcc    2640
ctcaaggacc tcaattccgt acctttgaga gcaattcata tataggtaat gatggattac    2700
```

-continued

```
gtggatatcc agtttcaaaa ggttgtggca aagatcctgt gtcagagaaa aactatacag   2760
tgtctgcgct agaagatcaa gaaagcaatt ctaaattttt caatgatttt tggaaagcag   2820
ctctgatggg ctatggaagt ggactgtgtt ttggcatatc cataatatat ttcttgatct   2880
cgactggaaa tctaagatgg cttgcaagaa tcattgaaga actggaacac aaaattatta   2940
tgcaaaggag gaagaagcag cgaggtcaaa gaaattacag aagaagaaat aatcgcttct   3000
agacaagtta ccaaatacag aaagatttga tttcagaact tcaggtattc aagctaagct   3060
ctaacactta tcttttttta gtttattcta acaactaata tatagttttt ttttttatca   3120
acaaatactt attaacactt gatacaaatt gctagtaatc agttggaagc tgtgatatat   3180
aacaaaggct aaaatttat agttgtgtga ctcactttct tatttttca gattttcagg    3240 agccaagaat tagaagacgc tggtgtaaag gatttgcttc ttcctatgtt gcagcttatg   3300
attgttggat ttgattttta gttttataag gttttcttca gttgggaaaa tgtaatattt   3360
tgaattttga tgatatacaa taaatgttgt gtttgttgaa tgatctgtat gcatttatcg   3420
gatcaataat actcacctca aagaatctaa gagagttagc gcacgataga agagatagaa   3480
catacaaaga agaatacatt acaaccttgg gctttactgg ttatcttaca ccccaaagct   3540
t                                                                  3541
```

<210> SEQ ID NO 6
<211> LENGTH: 799
<212> TYPE: PRT
<213> ORGANISM: Lycopersicon esculentum

<400> SEQUENCE: 6

```
Met Met Met Val Thr Ser Lys Val Phe Ser Ser Leu Gln Phe Phe Thr
  1               5                  10                  15

Val Phe Tyr Leu Phe Thr Val Ala Phe Ala Ser Thr Glu Glu Ala Thr
                 20                  25                  30

Ala Leu Leu Lys Trp Lys Ala Thr Phe Lys Asn Gln Asn Asn Ser Phe
             35                  40                  45

Leu Ala Ser Trp Thr Thr Ser Ser Asn Ala Cys Lys Asp Trp Tyr Gly
         50                  55                  60

Val Val Cys Leu Asn Gly Arg Val Asn Thr Leu Asn Ile Thr Asn Ala
     65                  70                  75                  80

Ser Val Ile Gly Thr Leu Tyr Ala Phe Pro Phe Ser Ser Leu Pro Phe
                 85                  90                  95

Leu Glu Asn Leu Asp Leu Ser Asn Asn Asn Ile Ser Gly Thr Ile Pro
                100                 105                 110

Pro Glu Ile Gly Asn Leu Thr Asn Leu Val Tyr Leu Asp Leu Asn Thr
            115                 120                 125

Asn Gln Ile Ser Gly Thr Ile Pro Gln Ile Gly Ser Leu Ala Lys
        130                 135                 140

Leu Gln Ile Ile Arg Ile Phe Asn Asn His Leu Asn Gly Phe Ile Pro
145                 150                 155                 160

Glu Glu Ile Gly Tyr Leu Arg Ser Leu Thr Lys Leu Ser Leu Gly Ile
                165                 170                 175

Asn Phe Leu Ser Gly Ser Ile Pro Ala Ser Leu Gly Asn Met Thr Asn
            180                 185                 190

Leu Ser Phe Leu Phe Leu Tyr Glu Asn Gln Leu Ser Gly Phe Ile Pro
        195                 200                 205

Glu Glu Ile Gly Tyr Leu Arg Ser Leu Thr Lys Leu Ser Leu Asp Ile
    210                 215                 220
```

-continued

```
Asn Phe Leu Ser Gly Ser Ile Pro Ala Ser Leu Gly Asn Leu Asn Asn
225                 230                 235                 240

Leu Ser Phe Leu Tyr Leu Tyr Asn Asn Gln Leu Ser Gly Ser Ile Pro
            245                 250                 255

Glu Glu Ile Gly Tyr Leu Arg Ser Leu Thr Tyr Leu Asp Leu Lys Glu
            260                 265                 270

Asn Ala Leu Asn Gly Ser Ile Pro Ala Ser Leu Gly Asn Leu Asn Asn
            275                 280                 285

Leu Ser Arg Leu Tyr Leu Tyr Asn Asn Gln Leu Ser Gly Ser Ile Pro
290                 295                 300

Glu Glu Ile Gly Tyr Leu Ser Ser Leu Thr Asn Leu Tyr Leu Gly Asn
305                 310                 315                 320

Asn Ser Leu Ile Gly Leu Ile Pro Ala Ser Phe Gly Asn Met Arg Asn
            325                 330                 335

Leu Gln Ala Leu Phe Leu Asn Asp Asn Leu Ile Gly Glu Ile Pro
            340                 345                 350

Ser Phe Val Cys Asn Leu Thr Ser Leu Glu Leu Leu Tyr Met Pro Arg
            355                 360                 365

Asn Asn Leu Lys Gly Lys Val Pro Gln Cys Leu Gly Asn Ile Ser Asp
370                 375                 380

Leu Leu Val Leu Ser Met Ser Ser Asn Ser Phe Ser Gly Glu Leu Pro
385                 390                 395                 400

Ser Ser Ile Ser Asn Leu Thr Ser Leu Lys Ile Leu Asp Phe Gly Arg
            405                 410                 415

Asn Asn Leu Glu Gly Ala Ile Pro Gln Cys Phe Gly Asn Ile Ser Ser
            420                 425                 430

Leu Gln Val Phe Asp Met Gln Asn Asn Lys Leu Ser Gly Thr Leu Pro
            435                 440                 445

Thr Asn Phe Ser Ile Gly Cys Ser Leu Ile Ser Leu Asn Leu His Gly
            450                 455                 460

Asn Glu Leu Glu Asp Glu Ile Pro Trp Ser Leu Asp Asn Cys Lys Lys
465                 470                 475                 480

Leu Gln Val Leu Asp Leu Gly Asp Asn Gln Leu Asn Asp Thr Phe Pro
            485                 490                 495

Met Trp Leu Gly Thr Leu Pro Glu Leu Arg Val Leu Arg Leu Thr Ser
            500                 505                 510

Asn Lys Leu His Gly Pro Ile Arg Ser Ser Gly Ala Glu Ile Met Phe
            515                 520                 525

Pro Asp Leu Arg Ile Ile Asp Leu Ser Arg Asn Ala Phe Ser Gln Asp
530                 535                 540

Leu Pro Thr Ser Leu Phe Glu His Leu Lys Gly Met Arg Thr Val Asp
545                 550                 555                 560

Lys Thr Met Glu Glu Pro Ser Tyr Glu Ile Tyr Asp Ser Val Val
            565                 570                 575

Val Val Thr Lys Gly Leu Glu Leu Glu Ile Val Arg Ile Leu Ser Leu
            580                 585                 590

Tyr Thr Val Ile Asp Leu Ser Ser Asn Lys Phe Glu Gly His Ile Pro
            595                 600                 605

Ser Val Leu Gly Asp Leu Ile Ala Ile Arg Val Leu Asn Val Ser His
            610                 615                 620

Asn Ala Leu Gln Gly Tyr Ile Pro Ser Ser Leu Gly Ser Leu Ser Ile
625                 630                 635                 640
```

-continued

| | | | | | | | | | | | |
|---|---|---|---|---|---|---|---|---|---|---|---|
|Leu|Glu|Ser|Leu|Asp|Leu|Ser|Phe|Asn|Gln|Leu|Ser|Gly|Glu|Ile|Pro|
| | | | |645| | | | |650| | | | |655| |

Gln Gln Leu Ala Ser Leu Thr Phe Leu Glu Phe Leu Asn Leu Ser His
                660                 665                 670

Asn Tyr Leu Gln Gly Cys Ile Pro Gln Gly Pro Gln Phe Arg Thr Phe
            675                 680                 685

Glu Ser Asn Ser Tyr Ile Gly Asn Asp Gly Leu Arg Gly Tyr Pro Val
        690                 695                 700

Ser Lys Gly Cys Gly Lys Asp Pro Val Ser Glu Lys Asn Tyr Thr Val
705                 710                 715                 720

Ser Ala Leu Glu Asp Gln Glu Ser Asn Ser Lys Phe Phe Asn Asp Phe
                725                 730                 735

Trp Lys Ala Ala Leu Met Gly Tyr Gly Ser Gly Leu Cys Phe Gly Ile
                740                 745                 750

Ser Ile Ile Tyr Phe Leu Ile Ser Thr Gly Asn Leu Arg Trp Leu Ala
            755                 760                 765

Arg Ile Ile Glu Glu Leu Glu His Lys Ile Ile Met Gln Arg Arg Lys
        770                 775                 780

Lys Gln Arg Gly Gln Arg Asn Tyr Arg Arg Asn Asn Arg Phe
785                 790                 795

<210> SEQ ID NO 7
<211> LENGTH: 4123
<212> TYPE: DNA
<213> ORGANISM: Lycopersicon esculentum

<400> SEQUENCE: 7

| | | |
|---|---|---|
|atcgatttta gagtcattgc aatttaattt tatcaaaata tttgagcatg aaaaatttga|60|
|aatggaggtg tcataaaaat aaaatacccT ttacaacacg actttattga gttgacgata|120|
|gttcaagtag ggaaaataaa taacttatta tttgaatata aaacttgcaa aaaaaaaaaa|180|
|gtgatattca aatttaattc tgaccattat ctcttgatat tctttgctct tcatttattt|240|
|gaatattcat ttttcaaaag ttccacatca taagacatca aatatcaagt aggtcccata|300|
|aaaataaaat acccttctca acatgacaaa gaaagattga aaaatgacta acattttctc|360|
|aaagacaaaa acaaaacatg tgagagaaga gaattttgaa ccaaatgtat tatacactaa|420|
|gagtggtcat gatcattgtg tgataacaaa actatttttgg caactttgac tcagtccttg|480|
|gctaaattag acctctaaca caacagtcca aaagttgact tgagaatgac aacattttct|540|
|tccctgatag caaccaaatt agcaaatttg gaaaaaacgt gtgtcttgtt gatctttaat|600|
|tagtataagt tacgtacaat atcctattga atcggaaaca ataaactcaa actatgatga|660|
|tggttactag caaagtattc tcttcacttc agttttttcac tgttttctac ctctttacag|720|
|ttgcatttgc ttcgactgag gaggcaactg ccctcttgaa atggaaagca actttcaaga|780|
|accagaataa ttcctttttg gcttcatgga cgacaagttc taatgcatgc aaggactggt|840|
|atggagttgt atgcttgaat ggtagggtaa acacgttgaa tattacaaat gccagtgtca|900|
|ttggtacact ttatgctttt ccattttcat ccctcccttt tctcgagaat cttgatctta|960|
|gcaacaacaa tatctctggt accattccac ctgagattgg taatctcaca atcttgtct|1020|
|atcttgactt gaacaccaat cagatttcag gaacaattcc accacaaatc ggttcactag|1080|
|ccaagcttca gatcatccgc atatttaaca atcatttaaa tggctttatt cctgaagaaa|1140|
|taggttacct aaggtctctt actaagctat ctttgggtat caactttctt agtggttcta|1200|
|ttcctgcttc attgggcaat atgaccaact tgtctttttt atttctttat gaaaatcagc|1260|

-continued

```
tttctggctt tattcctgaa gaaataggtt acctaaggtc tcttactaag ctatctttgg    1320
atatcaactt tcttagtggt tccattcctg cttcattggg gaatctgaac aacttgtctt    1380
ttttgtatct ttacaataat cagctttctg gctctattcc tgaagaaata ggttacctca    1440
ggtcacttac taagctatct ttgggtatca actttcttag tggttccatt cctgcttcat    1500
tggggaatct aaacaacttg tctaggttgg atctttacaa taataagctt tctggctcta    1560
ttcctgaaga aataggttac ctaaggtctc ttacttacct agatttgggt gagaatgctc    1620
ttaatggctc tattcctgct tcattgggga atctaaacaa cttgtttatg ttgtatcttt    1680
acaataatca gctttctggc tctattcctg aagaataggt tacctaagg tctcttactt    1740 acctagattt gggtgagaat gctcttaatg gctctattcc tgcttcattg ggaatctaa    1800 acaacttgtc taggttggat ctttacaata taagcttttc tggctctatt cctgaagaaa    1860
taggttacct aaggtctctt acttacctag atttgggtga gaatgctctt aatggctcta    1920
ttcctgcttc attggggaat ctgaacaact gtttatgtt gtatctttac aataatcagc    1980
tttctggctc tattcctgaa gaaataggtt acctgagttc tcttactgaa ctatatttgg    2040
gtaataactc tcttaatggc tctattcctg cttcattggg gaatctgaac aacttgttta    2100
tgttgtatct ttacaataat cagctttctg gctctattcc tgaagaaata ggttacctga    2160
gttctcttac tgaactattt tgggtaata actctcttaa tggctctatt cctgcttcat    2220
tggggaatct aaacaacttg tctaggttgt atctttacaa taatcagctt tctggctcta    2280
ttcctgcttc atttggcaat atgagaaatc tgcaaactct gtttctcagt gataacgatc    2340
tcattgggga aattccttca tttgtgtgca atttgacatc actggaagtg ttgtatatgt    2400
cgagaaacaa tttgaaggga aaagttccgc aatgtttggg taatatcagt gaccttcaca    2460
ttttgtcgat gtcatctaat agtttcagag gagagctccc ttcatctatt ccaatttaa    2520 catcactaaa aatacttgat tttggcagaa acaatctgga gggagcaata ccacaatttt    2580
ttggcaatat tagtagcctc caggtttttg atatgcagaa taacaaactt tctgggactc    2640
ttccaacaaa ttttagcatt ggatgttcac tgataagtct caacttgcat ggcaatgaac    2700
tagcagatga aatccctcgg tctttggaca attgcaaaaa gctgcaagtt cttgatttag    2760
gagacaatca actcaacgac acatttccca tgtggttggg aactttgcca gagctgagag    2820
ttttaaggtt gacatcgaat aaattgcatg gacctataag atcatcaggg gctgaaatca    2880
tgtttcctga tctccgaatc atagatctct ctcgcaatgc attctcgcaa gacttaccaa    2940
cgagtctatt tgaacatttg aaagggatga ggacagttga taaacaatg gaggaaccaa    3000 gttatgaaag ctattacgat gactcggtgg tagttgtgac aaagggattg gagcttgaaa    3060
ttgtgagaat tctgtctttg tacacaatta tcgatctttc aagcaacaaa tttgaaggac    3120
atattccttc tgtcctggga gatctcattg cgatccgtgt acttaatgta tctcataatg    3180
cattgcaagg ctatatacca tcatcacttg gaagtttatc tatactggaa tcactagacc    3240
tttcgtttaa ccaactttcg ggagagatac cacaacaact gcttctctt acgtttcttg    3300 aagtcttaaa tctctcccac aattatctcc aaggatgcat ccctcaagga cctcaattcc    3360
gtacctttga gagcaattca tatgaaggta atgatggatt acgtggatat ccagtttcaa    3420
aaggttgtgg caaagatcct gtgtcagaga aaaactatac agtgtctgcg ctagaagatc    3480
aagaaagcaa ttctgaattt ttcaatgatt tttggaaagc agctctgatg ggctatgaa    3540 gtggactgtg tattggcata tccataatat atatcttgat ctcgactgga aatctaagat    3600
```

-continued

```
ggcttgcaag aatcattgaa gaactggaac acaaaattat cgtgcaaagg agaaagaagc    3660
agcgaggtca agaaattac agaagaagaa ataatcgctt ctagacaagt taccaataca    3720
gaaagatttg atttcagaac ttcaggtatt caagctaacc tctaacactt atctttttta    3780
gtttattcta acaactaata tatgtttttt tttttatcaa caaatactta ttaacgcttg    3840
agacaaattg ctagtaatca gttggaagtt gtgatatata acaaaggcta aaatttata    3900 gttgtgtgac tcactttctt attttttccag attttcagga gccaagaata agaagacgct    3960
ggtgtaaagg atttgcttct tcctgtgttg cagcttatga tgttggatta gattttttagt    4020 tttataagct tttcttcagt tgggaaaatg taatattatg aattttgatg atatacaata    4080
aatgttgtgt ttattgaatg atatgtatgc atttatcgga tcc                      4123
```

<210> SEQ ID NO 8
<211> LENGTH: 1016
<212> TYPE: PRT
<213> ORGANISM: Lycopersicon esculentum

<400> SEQUENCE: 8

```
Met Met Met Val Thr Ser Lys Val Phe Ser Ser Leu Gln Phe Phe Thr
  1               5                  10                  15

Val Phe Tyr Leu Phe Thr Val Ala Phe Ala Ser Thr Glu Glu Ala Thr
                 20                  25                  30

Ala Leu Leu Lys Trp Lys Ala Thr Phe Lys Asn Gln Asn Asn Ser Phe
             35                  40                  45

Leu Ala Ser Trp Thr Thr Ser Ser Asn Ala Cys Lys Asp Trp Tyr Gly
         50                  55                  60

Val Val Cys Leu Asn Gly Arg Val Asn Thr Leu Asn Ile Thr Asn Ala
 65                  70                  75                  80

Ser Val Ile Gly Thr Leu Tyr Ala Phe Pro Phe Ser Ser Leu Pro Phe
                 85                  90                  95

Leu Glu Asn Leu Asp Leu Ser Asn Asn Asn Ile Ser Gly Thr Ile Pro
            100                 105                 110

Pro Glu Ile Gly Asn Leu Thr Asn Leu Val Tyr Leu Asp Leu Asn Thr
        115                 120                 125

Asn Gln Ile Ser Gly Thr Ile Pro Pro Gln Ile Gly Ser Leu Ala Lys
    130                 135                 140

Leu Gln Ile Ile Arg Ile Phe Asn Asn His Leu Asn Gly Phe Ile Pro
145                 150                 155                 160

Glu Glu Ile Gly Tyr Leu Arg Ser Leu Thr Lys Leu Ser Leu Gly Ile
                165                 170                 175

Asn Phe Leu Ser Gly Ser Ile Pro Ala Ser Leu Gly Asn Met Thr Asn
            180                 185                 190

Leu Ser Phe Leu Phe Leu Tyr Glu Asn Gln Leu Ser Gly Phe Ile Pro
        195                 200                 205

Glu Glu Ile Gly Tyr Leu Arg Ser Leu Thr Lys Leu Ser Leu Asp Ile
    210                 215                 220

Asn Phe Leu Ser Gly Ser Ile Pro Ala Ser Leu Gly Asn Leu Asn Asn
225                 230                 235                 240

Leu Ser Phe Leu Tyr Leu Tyr Asn Asn Gln Leu Ser Gly Ser Ile Pro
                245                 250                 255

Glu Glu Ile Gly Tyr Leu Arg Ser Leu Thr Lys Leu Ser Leu Gly Ile
            260                 265                 270

Asn Phe Leu Ser Gly Ser Ile Pro Ala Ser Leu Gly Asn Leu Asn Asn
        275                 280                 285
```

-continued

```
Leu Ser Arg Leu Asp Leu Tyr Asn Asn Lys Leu Ser Gly Ser Ile Pro
    290                 295                 300
Glu Glu Ile Gly Tyr Leu Arg Ser Leu Thr Tyr Leu Asp Leu Gly Glu
305                 310                 315                 320
Asn Ala Leu Asn Gly Ser Ile Pro Ala Ser Leu Gly Asn Leu Asn Asn
                325                 330                 335
Leu Phe Met Leu Tyr Leu Tyr Asn Asn Gln Leu Ser Gly Ser Ile Pro
            340                 345                 350
Glu Glu Ile Gly Tyr Leu Arg Ser Leu Thr Tyr Leu Asp Leu Gly Glu
            355                 360                 365
Asn Ala Leu Asn Gly Ser Ile Pro Ala Ser Leu Gly Asn Leu Asn Asn
        370                 375                 380
Leu Ser Arg Leu Asp Leu Tyr Asn Asn Lys Leu Ser Gly Ser Ile Pro
385                 390                 395                 400
Glu Glu Ile Gly Tyr Leu Arg Ser Leu Thr Tyr Leu Asp Leu Gly Glu
                405                 410                 415
Asn Ala Leu Asn Gly Ser Ile Pro Ala Ser Leu Gly Asn Leu Asn Asn
                420                 425                 430
Leu Phe Met Leu Tyr Leu Tyr Asn Asn Gln Leu Ser Gly Ser Ile Pro
            435                 440                 445
Glu Glu Ile Gly Tyr Leu Ser Ser Leu Thr Glu Leu Tyr Leu Gly Asn
            450                 455                 460
Asn Ser Leu Asn Gly Ser Ile Pro Ala Ser Leu Gly Asn Leu Asn Asn
465                 470                 475                 480
Leu Phe Met Leu Tyr Leu Tyr Asn Asn Gln Leu Ser Gly Ser Ile Pro
                485                 490                 495
Glu Glu Ile Gly Tyr Leu Ser Ser Leu Thr Glu Leu Phe Leu Gly Asn
                500                 505                 510
Asn Ser Leu Asn Gly Ser Ile Pro Ala Ser Leu Gly Asn Leu Asn Asn
            515                 520                 525
Leu Ser Arg Leu Tyr Leu Tyr Asn Asn Gln Leu Ser Gly Ser Ile Pro
        530                 535                 540
Ala Ser Phe Gly Asn Met Arg Asn Leu Gln Thr Leu Phe Leu Ser Asp
545                 550                 555                 560
Asn Asp Leu Ile Gly Glu Ile Pro Ser Phe Val Cys Asn Leu Thr Ser
                565                 570                 575
Leu Glu Val Leu Tyr Met Ser Arg Asn Asn Leu Lys Gly Lys Val Pro
            580                 585                 590
Gln Cys Leu Gly Asn Ile Ser Asp Leu His Ile Leu Ser Met Ser Ser
            595                 600                 605
Asn Ser Phe Arg Gly Glu Leu Pro Ser Ser Ile Ser Asn Leu Thr Ser
        610                 615                 620
Leu Lys Ile Leu Asp Phe Gly Arg Asn Asn Leu Glu Gly Ala Ile Pro
625                 630                 635                 640
Gln Phe Phe Gly Asn Ile Ser Ser Leu Gln Val Phe Asp Met Gln Asn
                645                 650                 655
Asn Lys Leu Ser Gly Thr Leu Pro Thr Asn Phe Ser Ile Gly Cys Ser
            660                 665                 670
Leu Ile Ser Leu Asn Leu His Gly Asn Glu Leu Ala Asp Glu Ile Pro
            675                 680                 685
Arg Ser Leu Asp Asn Cys Lys Lys Leu Gln Val Leu Asp Leu Gly Asp
        690                 695                 700
```

```
Asn Gln Leu Asn Asp Thr Phe Pro Met Trp Leu Gly Thr Leu Pro Glu
705                 710                 715                 720

Leu Arg Val Leu Arg Leu Thr Ser Asn Lys Leu His Gly Pro Ile Arg
            725                 730                 735

Ser Ser Gly Ala Glu Ile Met Phe Pro Asp Leu Arg Ile Ile Asp Leu
        740                 745                 750

Ser Arg Asn Ala Phe Ser Gln Asp Leu Pro Thr Ser Leu Phe Glu His
    755                 760                 765

Leu Lys Gly Met Arg Thr Val Asp Lys Thr Met Glu Glu Pro Ser Tyr
770                 775                 780

Glu Ser Tyr Tyr Asp Asp Ser Val Val Val Thr Lys Gly Leu Glu
785                 790                 795                 800

Leu Glu Ile Val Arg Ile Leu Ser Leu Tyr Thr Ile Ile Asp Leu Ser
                805                 810                 815

Ser Asn Lys Phe Glu Gly His Ile Pro Ser Val Leu Gly Asp Leu Ile
            820                 825                 830

Ala Ile Arg Val Leu Asn Val Ser His Asn Ala Leu Gln Gly Tyr Ile
        835                 840                 845

Pro Ser Ser Leu Gly Ser Leu Ser Ile Leu Glu Ser Leu Asp Leu Ser
    850                 855                 860

Phe Asn Gln Leu Ser Gly Glu Ile Pro Gln Gln Leu Ala Ser Leu Thr
865                 870                 875                 880

Phe Leu Glu Val Leu Asn Leu Ser His Asn Tyr Leu Gln Gly Cys Ile
                885                 890                 895

Pro Gln Gly Pro Gln Phe Arg Thr Phe Glu Ser Asn Ser Tyr Glu Gly
            900                 905                 910

Asn Asp Gly Leu Arg Gly Tyr Pro Val Ser Lys Gly Cys Gly Lys Asp
        915                 920                 925

Pro Val Ser Glu Lys Asn Tyr Thr Val Ser Ala Leu Glu Asp Gln Glu
    930                 935                 940

Ser Asn Ser Glu Phe Phe Asn Asp Phe Trp Lys Ala Ala Leu Met Gly
945                 950                 955                 960

Tyr Gly Ser Gly Leu Cys Ile Gly Ile Ser Ile Ile Tyr Ile Leu Ile
                965                 970                 975

Ser Thr Gly Asn Leu Arg Trp Leu Ala Arg Ile Ile Glu Glu Leu Glu
            980                 985                 990

His Lys Ile Ile Val Gln Arg Arg Lys Lys Gln Arg Gly Gln Arg Asn
        995                 1000                1005

Tyr Arg Arg Arg Asn Asn Arg Phe
    1010                1015

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gctatctttg ggtatcaact t                                           21

<210> SEQ ID NO 10
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 10
agatgacatc gacaaaatgt g                                              21
```